US010264807B2

(12) United States Patent
Aleschko et al.

(10) Patent No.: US 10,264,807 B2
(45) Date of Patent: Apr. 23, 2019

(54) FUSARIUM TOXIN-CLEAVING POLYPEPTIDE VARIANTS, ADDITIVE CONTAINING SAME, USE OF SAME, AND METHOD FOR SPLITTING FUSARIUM TOXINS

(71) Applicant: ERBER AKTIENGESELLSCHAFT, Getzersdorf bei Traismauer (AT)

(72) Inventors: Markus Aleschko, Vienna (AT); Corinna Kern, Vienna (AT); Dieter Moll, Stockerau (AT); Eva Maria Binder, Tulln (AT); Gerd Schatzmayr, Tulln (AT)

(73) Assignee: ERBER AKTIENGESELLSCHAFT, Getzersdorf bei Traismauer (AT)

( * ) Notice: Subject to any disclaimer, the term of this patent is extended or adjusted under 35 U.S.C. 154(b) by 0 days.

(21) Appl. No.: 15/553,218

(22) PCT Filed: Feb. 24, 2015

(86) PCT No.: PCT/AT2015/000032
§ 371 (c)(1),
(2) Date: Aug. 24, 2017

(87) PCT Pub. No.: WO2016/134387
PCT Pub. Date: Sep. 1, 2016

(65) Prior Publication Data
US 2018/0235255 A1    Aug. 23, 2018

(51) Int. Cl.
*C12N 9/18* (2006.01)
*C12N 15/55* (2006.01)
*A23K 10/14* (2016.01)
*A23K 50/30* (2016.01)
*A23K 50/60* (2016.01)
*A23K 20/147* (2016.01)
*C12N 1/21* (2006.01)

(52) U.S. Cl.
CPC ............ *A23K 10/14* (2016.05); *A23K 20/147* (2016.05); *A23K 50/30* (2016.05); *A23K 50/60* (2016.05); *C12N 9/18* (2013.01)

(58) Field of Classification Search
None
See application file for complete search history.

(56) References Cited

U.S. PATENT DOCUMENTS

2011/0189755 A1*   8/2011   Moll .................. C12N 9/10
                                                   435/189

FOREIGN PATENT DOCUMENTS

| EP | 0 988 383 B1 | 10/2002 |
|----|----|----|
| EP | 1 860 954 B1 | 1/2012 |
| EP | 2 326 713 B1 | 11/2015 |
| WO | 92/12645 A1 | 8/1992 |
| WO | 00/04158 A2 | 1/2000 |
| WO | 2004/085624 A2 | 10/2004 |
| WO | 2010/031100 A1 | 3/2010 |

OTHER PUBLICATIONS

Uniprot, Accession No. D2D3B6, 2014, www.uniprot.org.*
Guo et al., Protein tolerance to random amino acid change, Proc. Natl. Acad. Sci. USA, 2004, 101, 9205-10.*
Shortle, The denatured state (the other half of the folding equation) and its role in protein stability, FASEB J., 1996, 10, 27-34.*
International Search Report, dated Sep. 21, 2015 (3 pages).
Heinl et al., "Degradation of fumonisin $B_1$ by the consecutive action of two bacterial enzymes" Journal of Biotechnology, Elsevier Science Publishers, vol. 145, No. 2, Jan. 15, 2010, pp. 120-129, cited in the ISR (10 pages).

* cited by examiner

*Primary Examiner* — Robert B Mondesi
*Assistant Examiner* — Todd M Epstein
(74) *Attorney, Agent, or Firm* — Jacobson Holman, PLLC

(57) ABSTRACT

The invention relates to *fusarium* toxin-cleaving polypeptide variants of a *fusarium* toxin carboxyl esterase with the SEQ ID NO:46. Each of the polypeptide variants has an amino acid sequence shortened by 47 amino acids at the N terminus, and the amino acid sequences have at least 70%, preferably 80%, in particular 100%, sequence identity, namely SEQ ID NO:1, to the amino acid sequence portion 48-540 of the SEQ ID NO:46. The invention also relates to isolated polynucleotides which code for the polypeptide variants, to a *fusarium* toxin-cleaving additive containing at least one polypeptide variant and optionally at least one auxiliary agent, to the use of the polypeptide variants or the additive, and to a method for hydrolytically cleaving at least one *fusarium* toxin.

20 Claims, No Drawings
Specification includes a Sequence Listing.

FUSARIUM TOXIN-CLEAVING POLYPEPTIDE VARIANTS, ADDITIVE CONTAINING SAME, USE OF SAME, AND METHOD FOR SPLITTING FUSARIUM TOXINS

BACKGROUND OF THE INVENTION

The present invention relates to *fusarium* toxin-cleaving polypeptide variants, an additive containing the same, and the use of said polypeptide variants and/or said additive, and to methods for cleaving *fusarium* toxins by said polypeptide variants and/or said additive containing said polypeptide variants.

Mycotoxins very frequently occur in agricultural, plant-based products, causing severe economic damage as a function of the type and concentration of the mycotoxin, in particular in foods or feeds produced from agricultural products and also in humans and animals nourished with such foods or feeds, such damage being extremely manifold. Numerous methods have already been developed, by which it has been attempted to render harmless, i.e. detoxify or degrade, mycotoxins in order to largely prevent any damage caused by mycotoxins in the fields of animal and human nutrition, animal breeding, the processing of feed and food products and the like.

A prominent group of mycotoxins comprises *fusarium* toxins, wherein the terms "*fusarium* toxin" or "*fusarium* toxins" are equivalent and each refer to at least one or several, or the totality of, the fumonisins produced by the mold fungus *Fusarium* sp. as well as derivatives and degradation products thereof, yet in particular to fumonisins A1-2 (FA1-2), fumonisins B1-4 (FB1-4), fumonisins C1, 2, 4 (FC1, FC2, FC4) and HFC1 and to partially hydrolyzed fumonisins FA1-2, FB1-4, FC1-2, FC4 and HFC1. Partially hydrolyzed fumonisins comprise just one tricarballylic acid residue, whereas FA1-2, FB1-4, FC1-2, FC4 and HFC1 comprise two tricarballylic acid residues. Moreover, the structurally similar *Alternaria alternata lycopersici* (AAL) toxins are also encompassed by the group of *fusarium* toxins, AAL toxins being subdivided into the groups AAL-TA1 (CAS No 79367-52-5), AAL-TA2 (CAS No 79367-51-4), AAL-TB1 (CAS No 176590-32-2) and AAL-TB2 (CAS No 176705-51-4). FA1-2, FB1-4, FC1-2, FC4 and HFC1 have the following structural formula:

| Fusarium toxin | R1 | R2 | R3 | R4 | R5 |
|---|---|---|---|---|---|
| FA1 | —OH | —OH | —CH2CO | —CH3 | —H |
| FA2 | —H | —OH | —CH2CO | —CH3 | —H |
| FB1 | —OH | —OH | —H | —CH3 | —H |
| FB2 | —H | —OH | —H | —CH3 | —H |
| FB3 | —OH | —H | —H | —CH3 | —H |
| FB4 | —H | —H | —H | —CH3 | —H |
| FC1 | —OH | —OH | —H | —H | —H |
| FC2 | —OH | —H | —H | —H | —H |
| FC4 | —H | —H | —H | —H | —H |
| HFC1 | —OH | —OH | —H | —H | —OH |

FB1 is the most frequently occurring toxin from the group of *fusarium* toxins, yet numerous derivatives and related molecules likewise having toxic effects in humans and animals are known. The diseases caused by the ingestion of mycotoxins in humans or animals are referred to as mycotoxicoses, in the case of *fusarium* toxins also as *fusarium* toxin mycotoxicoses. Thus, it is known that *fusarium* toxins impair the sphingolipid metabolism by interacting with the enzyme ceramide synthase. Sphingolipids not only are components of cell membranes, but also play an important role as signal and messenger molecules in many elementary cellular processes such as cell growth, cell migration and cell binding, in inflammatory processes or intracellular transport processes. Due to the impairment of the sphingolipid metabolism, *fusarium* toxins have been made responsible for the toxic effects on various animal species and also humans. It could, thus, be demonstrated that *fusarium* toxins have immunosuppressive effects, cancerogenically acting in rodents, and they have been associated with esophageal cancer and neural tube defects in humans due to epidemiologic data. They have been held responsible for the typical toxicosis caused by pulmonary edemas in various animal species, for instance in pigs. Examples of *fusarium* toxin mycotoxicoses include neurotoxic diseases such as the equine leucoencephalomalacia or porcine pulmonary edemas caused by fumonisin intoxication. Since the contamination with *fusarium* toxins is almost ubiquitous on various cereal crops and, in particular corn, nuts and vegetables, their strongly negative effects on the health of humans and animals are not to be neglected.

The microbial degradation of fumonisins has already been described in EP-A 1 860 954, according to which microorganisms are used to detoxify fumonisins and fumonisin derivatives by adding to feeds detoxifying bacteria or yeasts selected from precisely defined strains for detoxifying fumonisins.

Catabolic metabolic paths for the biological degradation of fumonisins and the genes and enzymes responsible therefor have already been described, too. Thus, EP 0 988 383, for instance, describes fumonisin-detoxifying compositions and methods, wherein the fumonisin-degrading enzymes used are above all produced in transgenic plants in which the detoxification of fumonisins is effected using an amine oxidase that requires molecular oxygen for its enzymatic activity.

Moreover, WO 2004/085624 describes transaminases, deaminases and aminomutases and methods for the enzymatic detoxification of aminated toxins, e.g. fumonisins. In this context, polypeptides possessing deaminase activity are used for detoxification.

The above-identified products or methods involve the drawback of requiring molecular oxygen, and optionally cofactors, for the detoxification of mycotoxins, wherein, in particular, the cited amino oxidases do not show any effect under oxygen-free reaction conditions.

EP-A 2 326 713 relates to an additive, and a method for preparing the same, by which it is possible to degrade fumonisins in an oxygen-independent and cofactor-free enzymatic reaction. The temperature stability of the enzyme described therein that is mainly responsible for the detoxification, namely a carboxylesterase, is, however, low such that the additive, or carboxylesterase of SEQ ID No. 46, is not suitable for applications at elevated temperatures.

In the food and feed industries, thermal treatments for the production of hygienized products with reduced microbial load are of great importance. In this respect, the pelletization of feeds is particularly wide-spread, already constituting a standardized process, for a plurality of reasons such as enhancing flowability, reducing dust formation, lowering microbial load, in particular of salmonellae. During the pelletizing process, the commodity is usually moistened by hot steaming, heated and subsequently pressed through a matrix under pressure. The use of polypeptides or enzymes as additives for pelletizing foods or feeds constitutes a technological challenge, since the enzymes or polypeptides, as a rule, are sensitive to elevated temperatures. The thermal treatment of enzymes or polypeptides may result in a reduction of their specific activities and/or in irreversible denaturation. A way of counteracting this is the encapsulation or coating of the proteins such as, for instance, described in WO 92/12645. It is thereby possible to protect proteins from thermal influences, yet this approach involves the risk that the proteins will not be released rapidly enough in the mouth-gastrointestinal system, and hence will take effect either too slowly or not at all. Due to their low temperature stability, the hitherto known polypeptides for detoxifying *fusarium* toxins cannot be admixed to feeds or foods that are to be pelletized without prior encapsulation or prior coating.

Technological processes in which the detoxification of *fusarium* toxins at elevated temperatures is essential include the production of pasta and other corn products such as polenta, popcorn, cornflakes, corn bread or tortillas, and starch liquefaction processes, saccharification processes or fermentation processes such as, in particular, the mashing or fermentation process in the production of bioethanol. In this respect, it is important to ensure that foods or feeds produced by such processes do not contain *fusarium* toxins in harmful amounts. Hitherto known polypeptides cannot be used in such processes due to their minimal, or absent, activity at the process temperatures in question.

Hence there is the need for enzymes and/or polypeptides for the specific, safe and reliable cleavage, in particular detoxification, of *fusarium* toxins, wherein the enzymatic reaction requires neither oxygen nor a cofactor and the enzyme or polypeptide, moreover, exhibits sufficient temperature stability and sufficient temperature activity so as to be usable in technological processes at elevated temperatures.

BRIEF SUMMARY OF THE INVENTION

The present invention, therefore, aims to provide *fusarium* toxin-cleaving polypeptide variants of a *fusarium* toxin carboxylesterase of SEQ ID No. 46, by which it is possible to cleave at least one *fusarium* toxin to non-toxic or less toxic products in an oxygen-independent and cofactor-free manner, wherein the polypeptide variants have increased temperature stabilities and increased temperature activities as compared to *fusarium* toxin carboxylesterase of SEQ ID No. 46.

To solve this object, the present invention is essentially characterized by *fusarium* toxin-cleaving polypeptide variants of a *fusarium* toxin carboxylesterase of SEQ ID No. 46, characterized in that the polypeptide variants each possess an amino acid sequence truncated by 47 amino acids at the N-terminus, the amino acid sequences sharing at least 70%, preferably 80%, particularly preferably 100%, sequence identity, namely SEQ ID No. 1, with the amino acid sequence section 48-540 of SEQ ID No. 46, that the temperature stability (T(50%) of the polypeptide of SEQ ID No. 46 is determined to be 42° C. and that of the polypeptide variant of SEQ ID No. 1 is determined to be 45°, or modifications of SEQ ID No. 1 having a relative increase of T(50%) compared to the parental enzyme of SEQ ID No. 1, wherein on at least one position selected from the group consisting of 10, 33, 66, 107, 140, 144, 149, 151, 157, 199, 266, 267, 270, 272, 275, 280, 284, 286, 293, 302, 312, 329, 332, 360, 363, 364, 365, 367, 371, 372, 377, 389, 391, 394, 418, 419, 424, 427, 429, 430, 436, 440, 443, 447, 453, 455, 456, 457, 462, 463, 464, 465, 469, 473, 478, 487 and 490 an amino acid substitution is contained as modification, and that the amino acid substituents at positions 10 and 456 are selected from Q, E, N, H, K and R, at positions 33, 107, 293 and 332 from E, Q, D, K, R and N, at positions 66, 463 and 478 from D, E, K, N, Q and R, at positions 140 and 490 from P, A, S and N, at positions 144 and 367 from I, L, M and V, at positions 149, 270, 312, 329 and 372 from F, Y, W and H, at positions 151 and 453 from D, E, K and R, at positions 157 and 462 from F, H, W and Y, at positions 199, 302, 365 and 464 from I, L, M and V, at positions 266 and 455 and from A, S and T, at positions 267, 394 and 429 from A, N, P and S, at position 272 from H, N, Q and S, at position 275 from A, D, E, G, K, N, Q, R and S, at position 280 from A, D, E, K, N, P, Q, R and S, at position 284 from A, N, P, S, T and V, at position 286 from A, D, E, K, N, P, R and S, at positions 360, 377, 391, 419 and 427 from A, I, L S, T and V, at positions 363, 443 and 457 from A, S, T and V, at position 364 from H, I, L, M, N, Q, S and V, at position 371 from A, I, L, M, S, T and V, at position 389 from I, L, M and V, at positions 418, 430, 447 and 473 from A, G and S, at position 424 from A, D, E, G, K, R and S, at position 436 from A, G, S and T, at position 440 from A, G, S and T, at position 465 from A, G, H, N, Q, S and T, at position 469 from D, E, K and R and/or at position 487 from N, D, Q, H and S. It has surprisingly turned out that an amino acid sequence truncated by 47 amino acids relative to SEQ ID No. 46 is both significantly more active than said sequence and also has increased temperature stability as compared to said sequence. In that polypeptide variants of SEQ ID No. 1 are formed, in particular polypeptide variants having amino acid sequences sharing at least 70% sequence identity with SEQ ID No. 1, and comprising amino acid substitutions on at least one position selected from the group consisting of 10, 33, 66, 107, 140, 144, 149, 151, 157, 199, 266, 267, 270, 272, 275, 280, 284, 286, 293, 302, 312, 329, 332, 360, 363, 364, 365, 367, 371, 372, 377, 389, 391, 394, 418, 419, 424, 427, 429, 430, 436, 440, 443, 447, 453, 455, 456, 457, 462, 463, 464, 465, 469, 473, 478, 487 and 490, a temperature stability enhancement by at least 4% as compared to that of the *fusarium* toxin carboxylesterase of SEQ ID No. 1 has been achieved. The use of such polypeptide variants having *fusarium* toxin-cleaving properties has enabled the detoxification of *fusarium* toxins at elevated temperatures, for instance during technological processes. This is, in particular, enabled by the temperature activity being also enhanced in addition to the temperature stability. In particular, it will thereby be safeguarded that the enzymatic activity of the polypeptide variants will even be maintained at elevated temperature stresses as might, for instance, also occur during transport in containers.

According to the invention, a particularly strong increase in the temperature stability is achieved in that the amino acid substituents at positions 10 and 456 are selected from Q, E, N, H, K and R, at positions 33, 107, 293 and 332 from E, Q, D, K, R and N, at positions 66, 463 and 478 from D, E, K, N, Q and R, at positions 140 and 490 from P, A, S and N, at positions 144 and 367 from I, L, M and V, at positions 149, 270, 312, 329 and 372 from F, Y, W and H, at positions 151 and 453 from D, E, K and R, at positions 157 and 462 from F, H, W and Y, at positions 199, 302, 365 and 464 from I, L, M and V, at positions 266 and 455 and from A, S and T, at positions 267, 394 and 429 from A, N, P and S, at position 272 from H, N, Q and S, at position 275 from A, D, E, G, K, N, Q, R and S, at position 280 from A, D, E, K, N, P, Q, R and S, at position 284 from A, N, P, S, T and V, at position 286 from A, D, E, K, N, P, R and S, at positions 360, 377, 391, 419 and 427 from A, I, L S, T and V, at positions 363, 443 and 457 from A, S, T and V, at position 364 from H, I, L, M, N, Q, S and V, at position 371 from A, I, L, M, S, T and V, at position 389 from I, L, M and V, at positions 418, 430, 447 and 473 from A, G and S, at position 424 from A, D, E, G, K, R and S, at position 436 from A, G, S and T, at position 440 from A, G, S and T, at position 465 from A, G, H, N, Q, S and T, at position 469 from D, E, K and R, and/or at position 487 from N, D, Q, H and S, whereat the amino acids originally present on the cited positions having been substituted in any event.

The term "carboxylesterase" refers to any enzyme, polypeptide or polypeptide variant capable of cleaving carboxylic ester compounds to the respective alcohol compounds and carboxylic acid compounds by means of water. The term "*fusarium* toxin carboxylesterase" refers to any enzyme, polypeptide or polypeptide variant capable of hydrolyzing at least one *fusarium* toxin by hydrolytically cleaving at least one tricarballylic acid (propane-1,2,3-tricarboxylic acid) off the same. A "*fusarium* toxin-cleaving property" as described herein refers to the capability of hydrolytically cleaving off at least one tricarballylic acid residue from a least one *fusarium* toxin, in particular from FA1-2, FB1-4, FC1-2, FC4, HFC1, AAL-TA1-2 and AAL-TB1-2 or derivatives or degradation products thereof.

The terms used below are taken from the technical terminology and, unless otherwise stated, are each used in their conventional meanings. Thus, the term "polynucleotide" refers to any kind of genetic material of any length and sequence, such as single-stranded and double-stranded DNA and RNA molecules, including regulatory elements, structural elements, groups of genes, plasmids, entire genomes and fragments thereof. The term "polypeptide" comprises proteins such as enzymes, antibodies and polypeptides with up to 500 amino acids, such as peptide inhibitors, domains of proteins, yet even short polypeptides with small sequence lengths, e.g. less than 10 amino acids, such as receptors, ligands, peptide hormones, tags and the like. The term "position" in a polynucleotide or polypeptide refers to a single, specific base or amino acid in the sequence of said polynucleotide or polypeptide, respectively. The names of the amino acids are abbreviated by the one- or three-letter codes familiar to the skilled person in the art.

The term "unit" or "U" refers to the measure of the catalytic activity of an enzyme, polypeptide or polypeptide variant and is defined as the number of micromoles (μmol) of substrate, i.e. fumonisin B1 in this case, that are reacted or cleaved per minute under defined conditions. Thus, if at least one tricarballylic acid residue is cleaved off from 60 μmol FB1 within 15 min, this corresponds to a catalytic activity of 4 units. For FB1 cleavage, the reaction conditions are defined as follows: The reaction is carried out in 20 mM Tris-HCl buffer (pH 8.0) with 0.1 mg/ml bovine serum albumin at a temperature of 30° C. for 30 min. The substrate concentration in the reaction is 100 μM FB1.

By "catalytic activity", "catalytic enzyme activity" or "activity" of an enzyme or polypeptide solution or solution of a polypeptide variant, the enzymatic concentration of the enzyme or polypeptide solution, or solution of the polypeptide variant, is defined, indicated in units per milliliter of solution.

The term "specific activity" is defined as the catalytic activity per milligram of enzyme, polypeptide or polypeptide variant and is calculated from the ratio of the catalytic activity of an enzyme solution to the mass concentration (mass per unit volume) of the enzyme in said solution. If, for instance, an enzyme solution has a catalytic activity of 50 U/ml and a mass concentration of 1 mg/ml, its specific activity is 50 U/mg.

The term "temperature stability" refers to the property of enzymes, polypeptides or polypeptide variants to maintain their catalytic activities after temporary exposure to elevated temperatures (preincubation). The temperature stability is determined by measuring, and comparing, the activity of an enzyme or polypeptide solution, or solution of a polypeptide variant, after a 5-minute heat treatment and without heat treatment at identical, defined conditions. The temperature stability is thus a measure for the resistance of enzymes to temporal heat exposure. The temperature at which the residual activity of the heat-treated enzyme is 50% as compared to the non-heat-treated 100% control is the measure for the temperature stability and is abbreviated by T(50%). If, for instance, the activity of an enzyme solution is 50 U/ml without preincubation and 25 U/ml after a 5-minute preincubation at 50° C., the temperature stability of the enzyme is 50° C., or the enzyme is temperature-stable up to 50° C. The increases in the T(50%) of polypeptide variants relative to the parental polypeptide of SEQ ID No. 1 is defined as a measure for the increased temperature stability and can be indicated relatively as a percentage value or absolutely in degree Celsius.

The term "temperature activity" defines the temperature at which the enzyme, polypeptide or polypeptide variant exhibits the highest activity, the catalytic activity being measured over a period of 30 minutes.

The terms "polypeptide variant" or "variant", in particular, refer to polypeptide sequences possessing at least one amino acid substitution as compared to SEQ ID No. 46, wherein the enzymatic function, i.e. the *fusarium* toxin-cleaving property, remains maintained. Moreover, a "polypeptide variant" may additionally comprise amino acid insertions or deletions, in particular a C- or N-terminally extended or truncated sequence, relative to the polypeptide sequence of SEQ ID No. 46. An enzymatic function is substantially maintained if the enzymatic reaction mechanism remains unchanged, i.e. the *fusarium* toxin is hydrolyzed on the same site and the specific activity of the variant is at least 10%, preferably at least 50%, more preferably at least 90%, yet in particular >100%, based on the original, parental polypeptide of SEQ ID No. 46.

Amino acid substitutions at defined positions are described by the following nomenclature: original amino acid; position; new amino acid. If, for instance, glycine substitutes for a proline at position 134, this is indicated by Pro134Gly or P134G. Multiple mutations are separated by a plus sign or a slash. If, for instance, proline is substituted by glycine at position 134, and arginine is substituted by lysine at position 136, this is indicated by Pro134Gly+Arg136Lys or Pro134Gly/Arg136Lys or P134G+R136K or P134G/R136K, respectively. If an amino acid is substituted by two or several alternative amino acids at one position, the alternative amino acids are separated by a comma or a slash. If, for instance, proline is substituted at position 134 not only by glycine, but also by serine, valine and methionine, this is indicated by Pro134Gly,Ser, Val,Met or Pro134Gly/Ser/Val/Met or P134G,S,V,M or P134G/S/V/M. If, for instance, a substitution or exchange of an amino acid at a defined position is not defined in detail, this is to be interpreted such that said amino acid may be replaced by any other amino acid. If, for instance, a mutation of proline at position 134 is not defined in detail, the proline can be substituted by one of the following amino acids: A, R, N, D, C, Q, E, G, H, I, L, K, M, F, S, T, W, Y or V.

The term "sequence identity" refers to a percentual sequence identity. For amino acid sequences and nucleotide sequences, the sequence identity can be determined visually, yet preferably calculated by a computer program. The amino acid sequence having the sequence SEQ ID No. 1 is defined as reference sequence. A sequence comparison is also performed within sequence sections, a section meaning a continuous sequence of the reference sequence. Normally, the length of the sequence sections for nucleotide sequences is 18 to 600, preferably 45 to 200, more preferably 100 to 150, nucleotides. Normally, the length of the sequence sections for peptide sequences is 3 to 200, more preferably 15 to 65, most preferably 30 to 50, amino acids. There is a plurality of purchasable or costlessly available bioinformatic programs that can be used for the determination of homology and are constantly updated. Examples include GCG Wisconsin Besffit package (Devereux et al. 1984), BLAST (Altschul et al. 1990) or BLAST 2 (Tatusova and Madden 1999). Due to the different adjustment options of these algorithms, it may happen that different results are output at identical input sequences. It is, therefore, necessary to define the search algorithm and its respective settings. In the present case, the sequence identity was assessed using the programs NCBI BLAST (Basic Local Alignment Search Tool), in particular BLASTP for polypeptides and BLASTN for polynucleotides, which are available on the website of the National Center for Biotechnology Information (NCBI; http://www.ncbi.nlm.nih.gov/). It is thereby possible to compare two or several sequences with one another according to the algorithm of Altschul et al., 1997 (Nucleic Acids Res., 25:3389-3402). In this case, the program versions of Aug. 12, 2014, were used. As program settings, the base settings were applied, in particular for the amino acid comparison: "max target sequence"=100; "expected threshold"=10; "word size"=3; "matrix"=BLOSOM62; "gap costs"="Existence: 11; Extension: 1"; "computational adjustment"="Conditional compositional score matrix adjustment"; and for the nucleotide sequence comparison: Word Size: 11; Expect value: 10; Gap costs: Existence=5, Extension=2; Filter=low complexity activated; Match/Mismatch Scores: 2-3; Filter String: L; m.

According to a preferred further development of the invention, the amino acid substitution is selected from the group consisting of 10Q, 33E, 66D, 107E, 140P, 144M, 149F, 151R, 157Y, 199I, 266S, 267P, 270E, 272H, 275E, 275A, 280D, 280P, 284T, 284P, 286P, 286R, 293E, 302I, 312F, 329F, 332E, 360V, 363T, 364H, 364L, 365I, 367H, 371V, 371M, 372F, 377V, 389L, 391V, 394P, 418A, 419V, 424A, 424K, 427V, 429P, 430A, 436A, 436S, 440G, 440S, 443T, 447A, 453R, 455S, 456Q, 457T, 462Y, 463D, 464I, 465H, 465S, 465G, 469K, 473A, 478D, 487N and 490P. In that the polypeptide variants comprise at least one such substitution, the temperature stability and the temperature activity can even be more selectively enhanced, wherein other enzyme parameters such as the specific activity, pH stability or pH activity can likewise be improved, which, however, at least exhibit the values of the *fusarium* toxin carboxylesterase of SEQ ID No. 1.

According to a further development of the invention, the polypeptide variants on at least one position selected from the group consisting of 66, 199, 302, 377, 394, 424, 430 and 463 each comprise an amino acid substitution and a temperature stability increased by at least 6% as compared to that of *fusarium* toxins carboxylesterase of SEQ ID No. 1. Such polypeptide variants enable the cleavage of *fusarium* toxins during technological processes at elevated temperatures, such as the production of pasta and other corn products such as polenta, popcorn, cornflakes, corn bread or tortillas, and starch liquefaction processes, saccharification processes or fermentation processes such as, in particular, the mashing or fermentation process in the production of bioethanol.

According to a preferred further development of the invention, the amino acid substitution is selected from the group consisting of 66D, 199I, 302I, 377V, 394P, 424A, 430A and 463D. Such a substitution enables an increase of the temperature stability and of the temperature activity of the polypeptide variants by at least 3° C. relative to the *fusarium* toxin carboxylesterase of SEQ ID No. 1.

According to a further development of the invention, the polypeptide variants, on at least two, in particular three, positions of the amino acid sequence, selected from the group consisting of 10, 33, 66, 107, 140, 144, 149, 151, 157, 199, 266, 267, 270, 272, 275, 280, 284, 286, 293, 302, 312, 329, 332, 360, 363, 364, 365, 367, 371, 372, 377, 389, 391, 394, 418, 419, 424, 427, 429, 430, 436, 440, 443, 447, 453, 455, 456, 457, 462, 463, 464, 465, 469, 473, 478, 487 and 490, each comprise an amino acid substitution, wherein the amino acid substitution being selected from the group consisting of 10Q, 66D, 144M, 151R, 199I, 266S, 267P, 272H, 275E, 275A, 280D, 284T, 286P, 286R, 293E, 302I, 360V, 363T, 364H, 364L, 365I, 367H, 371V, 371M, 372F, 377V, 389L, 391V, 394P, 418A, 419V, 424A, 424K, 427V, 429P, 430A, 436A, 436S, 440G, 440S, 443T, 447A, 453R, 455S, 456Q, 457T, 462Y, 463D, 464I, 465H, 465S, 465G, 469K, 473A, 478D, 487N and 490P, and exhibit a temperature stability increased by at least 15% as compared to the *fusarium* toxin carboxylesterase of SEQ ID No. 1. It has surprisingly turned out that by substituting several amino acids their positive effects on the temperature stability are approximately additive, the temperature stability being increased by more than 7° C. by inserting at least three amino acids different from the amino acids originally present in the sequence. Such an increase is sufficient to use the enzymes, for instance, for mash resting at 55° C. in the production of bioethanol or to pelletize feeds at moderate temperatures of about 65 to 70° C.

According to a further development of the invention, the amino acid sequence of the polypeptide variants comprises combinations of several amino acid substitutions, the combinations of the positions being selected from the group consisting of 66/199/302/394/424/430, 66/199/302/377/394/424/430, 66/199/302/377/394/424/430/463, 66/144/199/302/360/372/377/394/424/430/443/463, 199/302/377/394/424/430/463, 66/199/302/377/394, 66/199/302/364/377/394/424/430/463, 66/199/302/377/394/424/430/463/465, 66/199/302/377/394/424/430/440/463, 66/199/302/377/394/424/430/447/463, 66/199/302/377/394/418/424/430/463, 66/199/302/377/394/424/436/430/463, 66/199/302/364/377/394/424/430/463, 66/199/302/377/394/424/430/463/490, 66/199/302/377/394/424/430/463/469, 66/199/302/377/389/394/424/430/463, 66/199/302/377/394/424/430/463/465, 66/199/302/377/394/424/430/463/464, 66/199/302/377/394/424/430/463/465, 66/199/302/377/394/424/430/440/463, 66/199/302/377/394/424/430/457/463, 66/199/302/377/394/424/430/436/463, 66/199/302/363/371/377/394/424/430/463, 66/199/302/377/394/424/430/447/453/463, 66/199/302/377/394/424/430/456/462/463, 66/199/302/377/394/419/424/427/430/463, 66/199/302/365/377/394/424/430/463/487 and 66/199/302/371/377/394/424/430/463/487. Polypeptide variants substituted in such a manner exhibit a temperature stability increased by at least 25% as compared to the *fusarium* toxin carboxylesterase of SEQ ID No. 1. Such combinations of substitutions enable a further increase of not only the temperature stability but also the temperature activity of the polypeptide variants.

According to a preferred further development of the invention, the amino acid sequences of the polypeptide variants are selected from the group consisting of SEQ ID Nos. 2 to 29. Such polypeptide variants have a temperature stability increased by at least 11° C., preferably at least 13° C., and even more preferably at least 15° C., as compared to the enzyme of SEQ ID No. 1, thus guaranteeing the activity of the respective polypeptide, and hence the detoxification of *fusarium* toxins, during or after technological processes at elevated temperature loads, such as mash resting at 65° C. in the production of bioethanol or pelletizing at temperatures of about 75-80° C.

According to a further development of the invention, each of the amino acid sequences of the polypeptide variants comprises combinations of several amino acid substitutions, the combinations of the positions being selected from the group consisting of 66/99/302/364/377/389/394/419/424/427/430/447/463/465/469, 66/199/302/377/389/394/419/424/427/430/447/463/465/469, 66/199/302/363/364/371/377/389/394/419/424/427/430/447/463/464/465/469, 66/199/302/363/371/377/389/394/419/424/427/430/447/463/464/465/469, 66/199/302/364/367/371/377/389/394/418/419/424/427/430/436/440/447/463/464/465/469/490, 66/199/302/367/371/377/389/394/418/419/424/427/430/436/440/447/463/464/465/469/490, 66/199/302/363/367/371/377/394/424/430/463/490, 66/199/302/377/394/418/419/424/427/430/436/440/447/463, 66/199/302/377/389/394/424/430/457/463/464/465/469, 66/199/302/363/371/377/389/394/419/424/427/430/440/447/457/463/464/469/490, 66/199/302/377/394/424/430/463/447/490/469/465, 66/199/302/377/394/424/430/463/490/469/465/419/427/371/487, 66/199/302/371/377/394/419/424/427/430/447/453/463/465/469/487/490, 66/199/302/367/371/377/389/394/418/419/424/427/429/430/436/440/447/457/463/464/465/469/490, 66/199/302/371/377/389/394/419/424/427/430/436/447/453/456/462/463/465/469/490/487 and 66/199/302/367/371/377/389/394/418/419/424/427/429/430/436/440/447/453/456/457/462/463/464/465/469/487/490. These polypeptide variants exhibit a temperature stability increased by at least 40%, and an increased temperature activity, as compared to the *fusarium* toxin carboxylesterase of SEQ ID No. 1 so as to be usable in a plurality of methods requiring elevated temperatures.

According to a preferred further development of the invention, the amino acid sequences of the polypeptide variants are selected from the group consisting of SEQ ID Nos. 30 to 45. Such polypeptide variants exhibit temperature stabilities increased by at least 18%, preferably at least 22° C., and more preferably at least 27° C., as compared to the enzyme of SEQ ID No. 1, thus ensuring an activity of the polypeptide, and hence the detoxification of *fusarium* toxins, during or after technological processes at high temperature loads, such as pelletizing at temperatures above 80° C., in particular above 85-90° C. Pelletizing at high temperatures of about 90° C. is of great importance, in particular, in the poultry industry in order to ensure a satisfactory reduction of the *salmonella* load on feed.

The term "conservative mutation" refers to the substitution of amino acids by other amino acids that are considered as conserved by a person skilled in the art, i.e. have similar specific properties, or the properties of the amino acid is maintained, i.e. conserved. Specific properties of amino acids are, for instance, their sizes, polarities, hydrophobicities, charges or pKa values. Amino acids can be classified in groups based on their properties, and the groups can be illustrated in the Venn Diagram. Amino acids from the same group, and preferably from the same subgroup, may be substituted for each other. The classification of amino acids according to the properties: hydrophobicity, polarity and size in groups and subgroups can be taken from Taylor W. R. (1986). By a conservative or conserved mutation, a substitution of an acidic amino acid for another acidic amino acid, a basic amino acid for another basic amino acid, a polar amino acid for another polar amino acid and the like are, for instance, understood. The polypeptide variants, in particular, may additionally contain at least one conservative amino acid substitution on at least one position, said conservative amino acid substitution being selected from the group of substitutions: G for A, A for G/S, V for I/L/A/T/S, I for V/L/M, L for I/M/V, M for L/I/V, P for A/S/N, F for Y/W/H, Y for F/W/H, W for Y/F/H, R for K/E/D, K for R/E/D, H for Q/N/S, D for N/E/K/R/Q, E for Q/D/K/R/N, S for T/A, T for S/V/A, C for S/T/A, N for D/Q/H/S and Q for E/N/H/K/R If a substitution in a polypeptide variant according to the invention at a defined position results in that, for instance, a polar amino acid such as Asp is replaced by a hydrophobic amino acid such as Ala, conserved mutations will also include any mutations leading to another hydrophobic amino acid (e.g. glycine, leucine, phenylalanine, valine) at that position. Such further polypeptide variants containing alternative conserved mutations are likewise encompassed.

The present invention further aims to provide polynucleotides encoding a *fusarium* toxin-cleaving polypeptide variant of a *fusarium* toxin carboxylesterase of SEQ ID No. 1, which enable the cleavage of at least one *fusarium* toxin to non-toxic or less toxic products in an oxygen-independent and cofactor-free manner and which exhibit an increased temperature stability as compared to the *fusarium* toxin carboxylesterase of SEQ ID No. 1.

To solve this object, the invention is characterized in that the polynucleotide comprises a nucleotide sequence encoding a *fusarium* toxin-cleaving polypeptide variant of a *fusarium* toxin carboxylesterase having the amino acid sequence SEQ ID No. 1, the polypeptide variants comprising an amino acid sequence sharing at least 70% sequence identity with the amino acid sequence SEQ ID No. 1, and that the polypeptide variants on at least one position selected from the group consisting of 10, 33, 66, 107, 140, 144, 149, 151, 157, 199, 266, 267, 270, 272, 275, 280, 284, 286, 293, 302, 312, 329, 332, 360, 363, 364, 365, 367, 371, 372, 377, 389, 391, 394, 418, 419, 424, 427, 429, 430, 436, 440, 443, 447, 453, 455, 456, 457, 462, 463, 464, 465, 469, 473, 478, 487 comprise an amino acid substitution, yet in particular the substitutions 10Q, 33E, 66D, 107E, 140P, 144M, 149F, 151R, 157Y, 199I, 266S, 267P, 270F, 272H, 275E, 275A, 280D, 280P, 284T, 284P, 286P, 286R, 293E, 302I, 312F, 329F, 332E, 360V, 363T, 364H, 364L, 365I, 367H, 371V, 371M, 372F, 377V, 389L, 391V, 394P, 418A, 419V, 424A, 424K, 427V, 429P, 430A, 436A, 436S, 440G, 440S, 443T, 447A, 453R, 455S, 456Q, 457T, 462Y, 463D, 464I, 465H, 465S, 465G, 469K, 473A, 478D, 487N and 490P or combinations thereof. Such an isolated polynucleotide, by using an expression vector, enables the generation of a transgenic host cell for the production of the polypeptide variants according to the invention.

The term "expression vector" refers to a DNA construct that is able to express a gene in vivo or in vitro. In particular, it encompasses DNA constructs suitable for transferring the polypeptide-encoding nucleotide sequence into the host cell so as to be integrated in the genome or freely located in the extrachromosomal space, and to intracellularly express the polypeptide-encoding nucleotide sequence and, optionally, transport the polypeptide out of the cell.

The term "host cell" refers to any cell that contains either a nucleotide sequence to be expressed, or an expression vector, and which is able to produce an enzyme or a polypeptide according to the invention. In particular, this refers to prokaryotic and/or eukaryotic cells, preferably *P. pastoris*, *E. coli*, *Bacillus subtilis*, *Streptomyces*, *Hansenula*, *Trichoderma*, *Lactobacillus*, *Aspergillus*, plant cells and/or spores of *Bacillus*, *Trichoderma* or *Aspergillus*. The name *Pichia pastoris* used herein is synonymous with the name *Komagataella pastoris*, *Pichia pastoris* being the older and *Komagataella pastoris* the systematically newer name (Yamada et al., 1995).

The present invention further aims to provide a *fusarium* toxin-cleaving additive containing at least one *fusarium* toxin-cleaving polypeptide variant of a *fusarium* toxin carboxylesterase having the amino acid sequence SEQ ID No. 46, the respective polypeptide variant cleaving at least one *fusarium* toxin to non-toxic or less toxic products in an oxygen-independent and cofactor-free manner and having an increased temperature stability as compared to the *fusarium* toxin carboxylesterase of SEQ ID No. 46.

To solve this object, the invention is characterized in that the *fusarium* toxin-cleaving additive comprises at least one polypeptide variant of a *fusarium* toxin carboxylesterase according to the invention and optionally at least one supplement material. By adding such an additive to *fusarium* toxin-contaminated feed, it has become possible to detoxify the *fusarium* toxins, which can be significantly measured by a reduction of the sphinganine to sphingosine ratio in the plasma and/or kidney and/or lung and/or liver of a subject fed with the additive.

The sphinganine to sphingosine ratio in various organs and in the plasma of animals is a generally accepted and sensitive biomarker for the toxic effects of *fusarium* toxins, in particular FB1. Disorders of the sphingolipid metabolism caused by *fusarium* toxins are inter alia associated with brain diseases of horses or lung edemas of pigs. The relevance of the sphinganine to sphingosine ratio as a biomarker and its analytical measurement is described in Grenier et al. (Biochem. Pharmaceuticals Vol. 83 (2012) p. 1465-1473) and in the EFSA Journal (2014; 12(5):3667).

According to a further development of the invention, the additive is formed such that the supplement material is selected from the group consisting of inert carriers, vitamins, minerals, phytogenic substances, enzymes and other components for detoxifying mycotoxins, such as mycotoxin-degrading enzymes, in particular aflatoxin oxidases, ergotamine hydrolases, ergotamine amidases, zearalenone esterases, zearalenone lactonases, zearalenone hydrolases, ochratoxin amidases, fumonisin aminotransferases, aminopolyol aminoxidases, deoxynivalenol epoxide hydrolases, deoxynivalenol dehydrogenases, deoxynivalenol oxidases, trichothecene dehydrogenases, trichothecene oxidases; mycotoxin-degrading microorganisms; and mycotoxin-binding substances, for instance microbial cell walls or inorganic materials such as bentonite. The use of such additives, for instance, in feed or food products, ensures that possibly contained amounts of *fusarium* toxins are reliably cleaved, in particular detoxified, to such an extent as to prevent any harmful effect on the organism of the subject ingesting such a feed or food product.

Further fields of application of the invention comprise additives containing, in addition to at least one polypeptide variant according to the invention, at least one enzyme which, for instance, participates in the degradation of proteins, e.g. proteases, or which is involved in the metabolism of starch or fibers or fat or glycogen, e.g. amylase, cellulose or glucanase, as well as, for instance, hydrolases, lipolytic enzymes, mannosidases, oxidases, oxidoreductases, phytases or xylanases.

The present invention, moreover, aims at the use of an additive according to the invention for cleaving at least one *fusarium* toxin in, in particular, pelletized food or feed products, in particular for pigs, poultry, cattle, horses, fishes or aquaculture. Any foods or feeds, in particular also distillers dried grains with solubles (DDGS), that are suitable for human or animal nutrition, in particular also for domestic animals, sheep or goats, can be used as foods or feeds.

The present invention, moreover, aims at the use of an additive according to the invention for cleaving at least one *fusarium* toxin in a process, in particular at temperatures of at least 50° C., for the production or processing of food or feed products. Such use of the additive ensures the detoxification of *fusarium* toxins, e.g. during food technological processes in which treatments at elevated temperatures are important, for instance in the processing of corn or grain, in starch liquefaction processes, in saccharification processes, or in fermentation processes such as the mashing or fermentation process in, in particular, the production of bioethanol. It will thereby be safeguarded that no relevant, in particular health-damaging, amounts of *fusarium* toxins will remain intact in any product originating from such a process, such as feed pellets, pasta, polenta, popcorn, cornflakes, corn bread, tortillas, DDGS or starch.

The present invention further aims to provide a polypeptide variant for use in a preparation for the prophylaxis and/or treatment of *fusarium* toxin mycotoxicoses. In the case of prophylaxis, it has become possible by the use of such a polypeptide variant or additive, despite the ingestion of *fusarium* toxins, to substantially maintain the health status of humans and animals at the level corresponding to that without, or reduced, oral ingestion of *fusarium* toxins. As regards the treatment of *fusarium* toxin mycotoxicoses, it has become possible to alleviate the symptoms of such a disease and, in particular, significantly improve the sphinganine to sphingosine ratio in organs and/or plasma. Moreover, such use will enable an enhancement of the capacity of livestock, in particular the feed conversion ratio and the gain in weight, as well as a reduction of the mortality rate.

Furthermore, the invention aims to provide a method for enzymatically cleaving at least one *fusarium* toxin, by which at least one *fusarium* toxin is hydrolytically cleaved by a polypeptide in an oxygen-independent, specific, safe and reliable manner to non-toxic or less toxic products, the hydrolytic cleavage occurring either during or after a temperature treatment.

To solve this object, the method is carried out such that at least one tricarballylic acid is hydrolytically cleaved off from the *fusarium* toxin by a polypeptide variant according to the invention, or an additive according to the invention. In doing so, the at least one *fusarium* toxin is mixed with at least one polypeptide variant according to the invention, or at least one additive according to the invention, at least one polypeptide variant hydrolytically cleaves at least one tricarballylic acid from the at least one *fusarium* toxin thus detoxifying the *fusarium* toxin, wherein the mixture of the respective polypeptide variant and the *fusarium* toxin is subjected to a temperature treatment of at least 50° C., preferably at least 70° C., and the hydrolytic cleavage is performed either during or after the temperature treatment.

In a preferred further development of the invention, the method is performed such that the polypeptide variant, or the additive, is mixed with a feed or food product contaminated with at least one *fusarium* toxin, and the temperature treatment is optionally performed by a pelletizing process. This will ensure that the *fusarium* toxins contained in the contaminated and optionally pelletized feed or food product will be cleaved as soon as the mixture of the polypeptide variant and the *fusarium* toxin has been contacted with moisture. With moist feeds or foods such as mashes or pulps, the hydrolysis of the *fusarium* toxins takes place in the moist feed or food prior to its oral ingestion. It will thereby be ensured that the harmful effects of *fusarium* toxins on humans and animals will be largely eliminated or at least reduced. By moisture, the presence of water or water-containing liquids is understood, this also including saliva or other liquids present in the digestive tract. The digestive tract is defined to comprise the mouth cavity, the pharynx (throat), the esophagus and the gastrointestinal tract or equivalents thereof, wherein different designations may be found with animals, or individual components may not be present in the digestive tracts of animals.

In a preferred further development of the invention, the method is conducted such that the polypeptide variant is used at a concentration range from 5 U to 500 U, preferably from 10 U to 300 U, and more preferably from 15 U to 100 U, per kilogram of feed or food product. By adding such amounts of the polypeptide variant, it has become possible, as a function of the concentration of the *fusarium* toxins, to cleave the latter in the food or feed product, in particular in DDGS, and thereby detoxify the same to such an extent that at least 70%, preferably at least 80%, in particular at least 90%, of the at least one *fusarium* toxin will be cleaved.

Unless otherwise specified, singular designations like "a" or "the" are to be understood as examples and shall comprise a plurality of options. If it is, for instance, referred to "a gene", "an enzyme" or "a cell", this shall always encompass the plural.

DETAILED DESCRIPTION OF THE INVENTION

In the following, the invention will be explained in more detail by way of examples.
Polypeptide Variants Example 1: Modification, Cloning and Expression of Polynucleotides Encoding *Fusarium* Toxin-Cleaving Polypeptides Amino acid substitutions, insertions or deletions were performed by mutations of the nucleotide sequences by means of PCR using the QuikChange site-directed mutagenesis kit (Stratagene) according to instructions. Alternatively, also complete nucleotide sequences were synthesized (GeneArt). The nucleotide sequences generated by PCR mutagenesis and those obtained from GeneArt were integrated by standard methods in expression vectors for the expression in *E. coli* or *P. pastoris*, were transformed in *E. coli* or *P. pastoris*, and were expressed in *E. coli* or *P. pastoris*, respectively (J. M. Cregg, *Pichia* Protocols, second Edition, ISBN-10: 1588294293, 2007; J. Sambrook et al. 2012, Molecular Cloning, A Laboratory Manual 4th Edition, Cold Spring Harbor), wherein any other suitable host cell may also be used for this task.

The term "expression vector" refers to a DNA construct capable of expressing a gene in vivo or in vitro. In particular, it encompasses DNA constructs suitable for transferring the polypeptide-encoding nucleotide sequence into the host cell so as to be integrated in the genome or freely located in the extrachromosomal space, and to intracellularly express the polypeptide-encoding nucleotide sequence and, optionally, transport the polypeptide out of the cell. The term "host cell" refers to any cell that contains either a nucleotide sequence to be expressed or an expression vector and is able to produce an enzyme or polypeptide according to the invention. In particular, this refers to prokaryotic and/or eukaryotic cells, preferably *P. pastoris*, *E. coli*, *Bacillus subtilis*, *Streptomyces*, *Hansenula*, *Trichoderma*, *Lactobacillus*, *Aspergillus*, plant cells and/or spores of *Bacillus*, *Trichoderma* oder *Aspergillus*. The soluble cell lysate in the case of *E. coli* and the culture supernatant in the case of *P. pastoris*, respectively, were used to determine the catalytic properties of the polypeptide variants.

Example 2: Determination of the Catalytic Activity and Specific Activity of *Fusarium* Toxin-Degrading Polypeptides The corresponding genes encoding *fusarium* toxin-degrading polypeptides were cloned in *Escherichia coli* using standard methods, intracellularly expressed, and subsequently lyzed by ultrasonic treatment and centrifuged. The clear supernatant was diluted with 20 mM Tris-HCl buffer (pH 8.0) containing 0.1 mg/l bovine serum albumin (about $10^{-3}$ to $10^{-5}$) and used in the FB1-degradation mixture so as to degrade 10% to 90% of the amount of FB1 contained in the degradation mixture by the polypeptide.

In order to determine the catalytic enzyme activity, tests on the hydrolytic cleavage of fumonisin B1 (FB1) were carried out, the tests having been performed in a 20 mM Tris-HCl buffer (pH 8.0) containing 0.1 mg/l bovine serum albumin at a temperature of 30° C. for 30 minutes. In addition, the mixture contained a substrate concentration of 100 µM FB1 (Biopure Referenzsubstanzen GmbH Tulin, Austria, BRM 001007) and one of the polypeptides to be tested. After an incubation of 30 minutes, the mixture was heat-inactivated at 99° C. for 5 min to stop the reaction.

In order to determine the enzymatic activity of feed samples, the *fusarium* toxin-transforming polypeptide variants have to be extracted from the feed samples prior to testing. To this end, 10 grams of feed were dissolved in 100 ml 20 mM Tris-HCl buffer (pH 8.0) containing 0.1 mg/ml bovine serum albumin and shaken at 150 rpm for 1 hour at 20° C. After this, the samples were centrifuged at 4000 g for 15 min, and the clear supernatant was diluted as required ($10^{-2}$ to $10^{-3}$) and used in the FB1 solution.

The quantification of FB1 was performed by LC-MS (liquid chromatography-mass spectroscopy) according to the method of Heinl et al. (J. of Biotechnology, 2010, 145, pp. 120-129, 2.6.3. "Liquid chromatography-mass spectrometry"). To this end, a calibration with FB1 standards additionally containing a complete $^{13}$C-labeled, internal FB1 standard (Biopure Referenzsubstanzen GmbH Tulin, Austria) was done. As opposed to Heinl et al. (2010), only the degradation of FB1 was measured to determine the catalytic enzyme activity of the polypeptide solutions used. The catalytic enzyme activity of the used polypeptide solutions is indicated in units per ml, one "unit" being defined as reduction of 1 µmol FB1 per minute under the above-identified reaction conditions in the test.

For determining the specific activities, the enzyme concentrations were determined by quantitative Western blot or ELISA. The specific enzyme activities were calculated by the activities (units) having been based on the used amounts of enzyme and are indicated in units per mg.

Example 3: Temperature Stability of *Fusarium* Toxin-Degrading Polypeptides

The expression and quantification of the *fusarium* toxin-degrading polypeptides were performed as described in Examples 1 and 2. Prior to the determination of the activity, the amount of cell lysate was divided into several portions (of 60 µl each). Two to 10 portions were subjected to a heat treatment for 5 min in a commercially available PCR cycler (e.g. Eppendorf Matercycler Gradient), each portion having been incubated at different temperatures. Meanwhile, another portion of the cell lysate, the 100% control, was incubated on ice. Following the heat treatment, all of the samples/test mixtures were incubated at 10° C. for 1 minute to equalize the temperatures. The enzymatic activity of both the heat-treated samples and the 100% control were determined as described in Example 2. The activity remaining after the heat treatment is referred to as residual activity. The temperature at which the residual activity is 50% as compared to the non-heat-treated 100% control, is abbreviated by T(50%), constituting the measure for the temperature stability of the polypeptide.

The increases of T(50%), indicated in degree Celsius, of polypeptide variants relative to the polypeptide of SEQ ID No. 46 or SEQ ID No. 1, respectively, is a measure for the increased temperature stability. The increase in the T(50%) value can be indicated in ° C., yet also in percent relative to the T(50%) value of the parental polypeptide. The following example serves for illustration: If the parental enzyme had a catalytic activity of 50 U/ml after a 5-minute incubation on ice and a catalytic activity of 25 U/ml after a 5-minute incubation at 48° C., the T(50%) value would be 48° C. If a polypeptide variant had a T(50%) value of 51° C., the relative increase in the temperature stability (T(50%)) would be 6.25. This results from the difference between the two T(50%) values of 3° C., divided by the T(50%) value of the parental starting enzyme of 48° C., multiplied by 100.

Instead of the catalytic activity, the specific activity may also be used for determining the temperature stability.

The determination of the temperature stability may also be performed by alternative enzymatic assays and even without determining the catalytic activity of the FB1 reaction. What is important in this respect, is that equal amounts of thermally treated polypeptide and of the 100% control are used, which is, for instance, ensured by the use of equal volumes of cell lysate.

Instead of the catalytic activity, also the measurement signals of enzymatic degradation assays (e.g. MS signal, extinction, etc.) may be used for determining the temperature stability. If the measurement signal is directly proportional to the enzymatic activity (e.g. peak surface of reacted FB1), the T(50%) value of a polypeptide is the temperature at which the value of the measurement signal of the heat-treated polypeptide comprises 50% of the value of the measurement signal of the 100% control of the polypeptide.

The temperature stability (T(50%)) of the polypeptide of SEQ ID No. 46 was determined to be 42° C., that of the polypeptide of SEQ ID No. 1 to be 45° C. Thus, the relative increase in the temperature stability that could be achieved by truncating the N-terminal sequence was about 7%. Moreover, an increase in the enzymatic activity of the polypeptide of SEQ ID No. 1 relative to the parental polypeptide of SEQ ID No. 46 could also be determined.

The temperature stability of the polypeptide of SEQ ID No. 1 could be further increased by the selective substitution of individual amino acids. The relative increases in the temperature stability of these polypeptide variants relative to the parental polypeptide of SEQ ID No. 1 are illustrated in Table 1.

TABLE 1

Modifications of the polypeptide variants and their relative increases in the temperature stability in percent as compared to the parental enzyme of SEQ ID No. 1

| Modification(s) of SEQ ID No. 1 | Relative increase in T (50%) | SEQ ID No. of the polypeptide containing the modifications |
|---|---|---|
| H10Q | 4.4% | — |
| A33E | 4.4% | — |
| N66D | 6.7% | — |
| G107E | 4.4% | — |
| I140P | 4.4% | — |
| L144M | 4.4% | — |
| L149F | 4.4% | — |
| K151R | 4.4% | — |
| V157Y | 4.4% | — |
| L199I | 6.7% | — |
| R266S | 4.4% | — |
| Q267P | 4.4% | — |
| K270F | 4.4% | — |
| R272H | 4.4% | — |
| G275E | 4.4% | — |
| G275A | 4.4% | — |
| G280D | 4.4% | — |
| G280P | 4.4% | — |
| R284T | 4.4% | — |
| R284P | 4.4% | — |
| L286P | 4.4% | — |
| L286R | 4.4% | — |
| K293E | 4.4% | — |
| L302I | 6.7% | — |
| A312F | 4.4% | — |
| L329F | 4.4% | — |

TABLE 1-continued Modifications of the polypeptide variants and their relative increases in the temperature stability in percent as compared to the parental enzyme of SEQ ID No. 1

| Modification(s) of SEQ ID No. 1 | Relative increase in T (50%) | SEQ ID No. of the polypeptide containing the modifications |
|---|---|---|
| Q332E | 4.4% | — |
| F360V | 4.4% | — |
| S363T | 4.4% | — |
| Q364H | 4.4% | — |
| Q364L | 4.4% | — |
| F365I | 4.4% | — |
| N367H | 4.4% | — |
| L371V | 4.4% | — |
| L371M | 4.4% | — |
| L372F | 4.4% | — |
| A377V | 6.7% | — |
| T389L | 4.4% | — |
| I391V | 4.4% | — |
| A394P | 6.7% | — |
| S418A | 4.4% | — |
| M419V | 4.4% | — |
| E424A | 6.7% | — |
| E424K | 4.4% | — |
| A427V | 4.4% | — |
| A429P | 4.4% | — |
| S430A | 6.7% | — |
| T436A | 4.4% | — |
| T436S | 4.4% | — |
| A440G | 4.4% | — |
| A440S | 4.4% | — |
| V443T | 4.4% | — |
| V447A | 4.4% | — |
| Q453R | 4.4% | — |
| T455S | 4.4% | — |
| K456Q | 4.4% | — |
| S457T | 4.4% | — |
| F462Y | 4.4% | — |
| E463D | 6.7% | — |
| R464I | 4.4% | — |
| R465H | 4.4% | — |
| R465S | 4.4% | — |
| R465G | 4.4% | — |
| M469K | 4.4% | — |
| S473A | 4.4% | — |
| G478D | 4.4% | — |
| K487N | 4.4% | — |
| Q490P | 4.4% | — |
| L199I/A394P | 13.3% | — |
| N66D/L199I | 11.1% | — |
| L199I/L302I | 13.3% | — |
| L199I/A377V | 15.6% | — |
| L199I/E424A | 11.1% | — |
| L199I/S430A | 11.1% | — |
| L199I/E463D | 13.3% | — |
| L199I/L302I/A394P | 20.0% | — |
| L199I/L302I/A377V | 17.8% | — |
| L199I/L302I/E424A | 17.8% | — |
| L199I/A377V/A394P | 22.2% | — |
| L199I/A394P/A429P | 17.8% | — |
| L372F/A394P/V443T | 17.8% | — |
| L199I/L302I/L372F | 15.6% | — |
| L144M/L199I/L302I | 20.0% | — |
| F360V/A394P/V443T | 17.8% | — |
| H10Q/K151R/A302I | 15.6% | — |
| R266S/A377V/E424K | 20.0% | — |
| Q267/A394P/T436S | 17.8% | — |
| R272H/G280D/E463D | 20.0% | — |
| G275A/L302I/F360V | 17.8% | — |
| N66D/L286P/N367H | 15.6% | — |
| R284T/L286R/S430A | 15.6% | — |
| K293E/E424A/M469K | 20.0% | — |
| S363T/A377V/K456Q | 20.0% | — |
| Q364H/L371V/S430A | 17.8% | — |
| L199I/Q364L/Q490P | 15.6% | — |
| F365I/A394P/R464I | 15.6% | — |
| L371M/A377V/A429P | 17.8% | — |
| L302I/L372F/Q453R | 15.6% | — |

TABLE 1-continued

Modifications of the polypeptide variants and their relative increases in the temperature stability in percent as compared to the parental enzyme of SEQ ID No. 1

| Modification(s) of SEQ ID No. 1 | Relative increase in T (50%) | SEQ ID No. of the polypeptide containing the modifications |
|---|---|---|
| T389L/M419V/E463D | 17.8% | — |
| I391V/A394P/A440G | 20.0% | — |
| S418A/S430A/F462Y | 20.0% | — |
| N66D/A427V/V443T | 17.8% | — |
| A440S/S457T/E463D | 20.0% | — |
| L199I/V447A/T455S | 20.0% | — |
| A377V/R465H/K487N | 17.8% | — |
| L302I/R465S/G478D | 15.6% | — |
| A377V/R465G/S473A | 20.0% | — |
| N66D/L199I/L302I/A394P/E424A/S430A | 26.7% | SEQ ID No. 2 |
| N66D/L199I/L302I/A377V/A394P/E424A/S430A | 31.1% | SEQ ID No. 3 |
| N66D/L199I/L302I/A377V/A394P/E424A/S430A/E463D | 37.8% | SEQ ID No. 4 |
| N66D/L144M/L199I/L302I/F360V/L372F/A377V/ A394P/E424A/S430A/V443T/E463D | 33.3% | SEQ ID No. 5 |
| L199I/L302I/A377V/A394P/E424A/S430A/E463D | 31.1% | SEQ ID No. 6 |
| N66D/L199I/L302I/A377V/A394P | 26.7% | SEQ ID No. 7 |
| N66D/L199I/L302I/Q364H/A377V/A394P/ E424A/S430A/E463D | 35.5% | SEQ ID No. 8 |
| N66D/L199I/L302I/A377V/A394P/E424A/ S430A/E463D/R465H | 40.0% | SEQ ID No. 9 |
| N66D/L199I/L302I/A377V/A394P/E424A/ S430A/A440G/E463D | 37.8% | SEQ ID No. 10 |
| N66D/L199I/L302I/A377V/A394P/E424A/ S430A/V447A/E463D | 35.5% | SEQ ID No. 11 |
| N66D/L199I/L302I/A377V/A394P/S418A/ E424A/S430A/E463D | 35.5% | SEQ ID No. 12 |
| N66D/L199I/L302I/A377V/A394P/E424A/ T436A/S430A/E463D | 35.5% | SEQ ID No. 13 |
| N66D/L199I/L302I/Q364L/A377V/A394P/ E424A/S430A/E463D | 35.5% | SEQ ID No. 14 |
| N66D/L199I/L302I/A377V/A394P/E424A/ S430A/E463D/Q490P | 37.8% | SEQ ID No. 15 |
| N66D/L199I/L302I/A377V/A394P/E424A/ S430A/E463D/M469K | 37.8% | SEQ ID No. 16 |
| N66D/L199I/L302I/A377V/T389L/A394P/ E424A/S430A/E463D | 40.0% | SEQ ID No. 17 |
| N66D/L199I/L302I/A377V/A394P/E424A/ S430A/E463D/R465S | 35.5% | SEQ ID No. 18 |
| N66D/L199I/L302I/A377V/A394P/E424A/ S430A/E463D/R464I | 40.0% | SEQ ID No. 19 |
| N66D/L199I/L302I/A377V/A394P/E424A/ S430A/E463D/R465G | 35.5% | SEQ ID No. 20 |
| N66D/L199I/L302I/A377V/A394P/E424A/ S430A/A440S/E463D | 33.3% | SEQ ID No. 21 |
| N66D/L199I/L302I/A377V/A394P/E424A/ S430A/S457T/E463D | 37.8% | SEQ ID No. 22 |
| N66D/L199I/L302I/A377V/A394P/E424A/ S430A/T436S/E463D | 35.5% | SEQ ID No. 23 |
| N66D/L199I/L302I/S363T/L371V/A377V/ A394P/E424A/S430A/E463D | 40.0% | SEQ ID No. 24 |
| N66D/L199I/L302I/A377V/A394P/E424A/ S430A/V447A/Q453R/E463D | 35.5% | SEQ ID No. 25 |
| N66D/L199I/L302I/A377V/A394P/E424A/ S430A/K456Q/F462Y/E463D | 40.0% | SEQ ID No. 26 |
| N66D/L199I/L302I/A377V/A394P/M419V/ E424A/A427V/S430A/E463D | 35.5% | SEQ ID No. 27 |
| N66D/L199I/L302I/F365I/A377V/A394P/ E424A/S430A/E463D/K487N | 33.3% | SEQ ID No. 28 |
| N66D/L199I/L302I/L371M/A377V/A394P/ E424A/S430A/E463D/K487N | 33.3% | SEQ ID No. 29 |
| N66D/L199I/L302I/Q364L/A377V/T389L/ A394P/M419V/E424A/A427V/S430A/V447A/E463D/ R465S/M469K | 51.1% | SEQ ID No. 30 |
| N66D/L199I/L302I/A377V/T389L/A394P/M419V/ E424A/A427V/S430A/V447A/E463D/R465S/ M469K | 46.7% | SEQ ID No. 31 |
| N66D/L199I/L302I/S363T/Q364L/L371V/ A377V/T389L/A394P/M419V/E424A/A427V/S430A/ V447A/E463D/R464I/R465S/M469K | 60.0% | SEQ ID No. 32 |
| N66D/L199I/L302I/S363T/L371V/A377V/T389L/ A394P/M419V/E424A/A427V/S430A/V447A/ E463D/R464I/R465S/M469K | 57.8% | SEQ ID No. 33 |

TABLE 1-continued

Modifications of the polypeptide variants and their relative increases in the temperature stability in percent as compared to the parental enzyme of SEQ ID No. 1

| Modification(s) of SEQ ID No. 1 | Relative increase in T (50%) | SEQ ID No. of the polypeptide containing the modifications |
|---|---|---|
| N66D/L199I/L302I/Q364L/N367H/L371V/A377V/ T389L/A394P/S418A/M419V/E424A/A427V/ S430A/T436A/A440S/V447A/E463D/R464I/ R465S/M469K/Q490P | 62.2% | SEQ ID No. 34 |
| N66D/L199I/L302I/N367H/L371V/A377V/T389 L/A394P/S418A/M419V/E424A/A427V/S430A/ T436A/A440S/V447A/E463D/R464I/R465S/ M469K/Q490P | 62.2% | SEQ ID No. 35 |
| N66D/L199I/L302I/S363T/N367H/L371V/ A377V/A394P/E424A/S430A/E463D/Q490P | 42.2% | SEQ ID No. 36 |
| N66D/L199I/L302I/A377V/A394P/S418A/ M419V/E424A/A427V/S430A/T436A/A440S/V447A/ E463D | 46.7% | SEQ ID No. 37 |
| N66D/L199I/L302I/A377V/T389L/A394P/E424A/ S430A/S457T/E463D/R464I/R465S/M469K | 48.9% | SEQ ID No. 38 |
| N66D/L199I/L302I/S363T/L371V/A377V/ T389L/A394P/M419V/E424A/A427V/S430A/A440S/ V447A/S457T/E463D/R464I/M469K/Q490P | 55.5% | SEQ ID No. 39 |
| N66D/L199I/L302I/A377V/A394P/E424A/S430A/ V447A/E463D/R465S/M469K/Q490P | 46.7% | SEQ ID No. 40 |
| N66D/L199I/L302I/L371M/A377V/A394P/ M419V/E424A/A427V/S430A/E463D/R465S/ M469K/K487N/Q490P | 51.1% | SEQ ID No. 41 |
| N66D/L199I/L302I/L371M/A377V/A394P/ M419V/E424A/A427V/S430AA/447A/Q453R/ E463D/R465S/M469K/K487N/Q490P | 55.5% | SEQ ID No. 42 |
| N66D/L199I/L302I/N367H/L371V/A377V/T389L/ A394P/S418A/M419V/E424A/A427V/A429P/ S430A/T436A/A440S/V447A/S457T/E463D/ R464I/R465S/M469K/Q490P | 64.4% | SEQ ID No. 43 |
| N66D/L199I/L302I/L371M/A377V/T389L/A394P/ M419V/E424A/A427V/S430A/T436A/V447A/ Q453R/K456Q/F462Y/E463D/R465S/M469K/ K487N/Q490P | 62.2% | SEQ ID No. 44 |
| N66D/L199I/L302I/N367H/L371V/A377V/T389L/ A394P/S418A/M419V/E424A/A427V/A429P/ S430A/T436A/A440S/V447A/Q453R/K456Q/ S457T/F462Y/E463D/R464I/R465S/M469K/ K487N/Q490P | 65.2% | SEQ ID No. 45 |

Example 4: Temperature-Dependent Activity (Temperature Activity) of *Fusarium* Toxin-Degrading Polypeptides The *fusarium* toxin-degrading polypeptide variants to be tested for their temperature-dependent activities were purified prior to carrying out the tests. To this end, the polypeptide variants were purified from fermentation supernatants in a two-step process using anion exchange chromatography and subsequently size exclusion chromatography. The polypeptide variants were adjusted to concentrations of 1 mg/ml and used in the reaction mixture at dilutions of $10^{-5}$ to $10^{-6}$ in reaction volumes of 1 ml. Activity determinations were performed by tests as described in Example 3, by FB1 hydrolysis and subsequent quantification of FB1 by LC-MS, the tests have been carried out at different temperatures. Incubation was performed using two heating blocks (Eppendorf, ThermoMixer) at temperatures of 10° C., 20° C., 30° C., 35° C., 40° C., 45° C., 50° C., 55° C., 60° C., 65° C. and 70° C. Thirty minutes after the beginning of the heat exposure, 100 µl of the reaction mixture were each taken and heat-inactivated at 99° C. for 5 min. The test performed at 30° C. in the heating block served as a 100% control. Exemplary results are indicated in Table 2.

TABLE 2

Temperature-dependent activities of fusarium toxin-degrading polypeptides. <LOQ values are below detection limits (level of quantification: <0.15 U/l in the test preparation)

| Sequence ID incl. amino acid substitutions | Temperature | Relative activity, based on the activity at 30° C. [%] |
|---|---|---|
| SEQ ID No. 1 | 10° C. | 35 |
| | 20° C. | 59 |
| | 30° C. | 100 |
| | 35° C. | 123 |
| | 40° C. | 100 |

TABLE 2-continued Temperature-dependent activities of fusarium toxin-degrading polypeptides. <LOQ values are below detection limits (level of quantification: <0.15 U/l in the test preparation)

| | | |
|---|---|---|
| | 45° C. | 105 |
| | 50° C. | 90 |
| | 55° C. | 26 |
| | 60° C. | <LOQ |
| | 65° C. | <LOQ |
| | 70° C. | <LOQ |
| SEQ ID No. 1 with | 30° C. | 100 |
| L199I/L302I/A394P | 40° C. | 100 |
| | 50° C. | 95 |
| | 60° C. | 62 |
| | 70° C. | 16 |
| SEQ ID No. 1 with | 30° C. | 100 |
| L144M/L199I/L302I | 40° C. | 104 |
| | 50° C. | 91 |
| | 60° C. | 60 |
| | 70° C. | 18 |
| SEQ ID No. 1 with | 30° C. | 100 |
| R266S/A377V/E424K | 40° C. | 110 |
| | 50° C. | 97 |
| | 60° C. | 63 |
| | 70° C. | 29 |
| SEQ ID No. 1 with | 30° C. | 100 |
| K293E/E424A/M469K | 40° C. | 98 |
| | 50° C. | 81 |
| | 60° C. | 50 |
| | 70° C. | <LOQ |
| SEQ ID No. 1 with | 30° C. | 100 |
| F365I/A394P/R464I | 40° C. | 105 |
| | 50° C. | 84 |
| | 60° C. | 57 |
| | 70° C. | 14 |
| SEQ ID No. 1 with | 30° C. | 100 |
| S418A/S430A/F462Y | 40° C. | 103 |
| | 50° C. | 89 |
| | 60° C. | 53 |
| | 70° C. | <LOD |
| SEQ ID No. 4 | 10° C. | 33 |
| | 20° C. | 58 |
| | 30° C. | 100 |
| | 35° C. | 109 |
| | 40° C. | 110 |
| | 45° C. | 114 |
| | 50° C. | 148 |
| | 55° C. | 113 |
| | 60° C. | 94 |
| | 65° C. | 83 |
| | 70° C. | 46 |
| SEQ ID No. 43 | 10° C. | 31 |
| | 20° C. | 56 |
| | 30° C. | 100 |
| | 35° C. | 113 |
| | 40° C. | 120 |
| | 45° C. | 126 |
| | 50° C. | 157 |
| | 55° C. | 168 |
| | 60° C. | 134 |
| | 65° C. | 102 |
| | 70° C. | 98 |
| SEQ ID No. 44 | 10° C. | 33 |
| | 20° C. | 59 |
| | 30° C. | 100 |
| | 35° C. | 110 |
| | 40° C. | 124 |
| | 45° C. | 131 |
| | 50° C. | 162 |
| | 55° C. | 174 |
| | 60° C. | 126 |
| | 65° C. | 99 |
| | 70° C. | 95 |
| SEQ ID No. 45 | 10° C. | 41 |
| | 20° C. | 68 |
| | 30° C. | 100 |
| | 35° C. | 115 |
| | 40° C. | 136 |
| | 45° C. | 141 |
| | 50° C. | 164 |

TABLE 2-continued

Temperature-dependent activities of fusarium toxin-degrading polypeptides. <LOQ values are below detection limits (level of quantification: <0.15 U/l in the test preparation)

| | 55° C. | 177 |
| --- | --- | --- |
| | 60° C. | 137 |
| | 65° C. | 121 |
| | 70° C. | 100 |

| Enzyme | Palletizing temperature | Residual activity % |
| --- | --- | --- |
| SEQ ID No. 1 | 75° C. | 15 |
| | 80° C. | <LOQ |
| | 85° C. | <LOQ |
| | 90° C. | <LOQ |
| SEQ ID No. 4 | 75° C. | 57 |
| | 80° C. | 46 |
| | 85° C. | 37 |
| | 90° C. | 14 |
| SEQ ID No. 43 | 75° C. | 78 |
| | 80° C. | 73 |
| | 85° C. | 58 |
| | 90° C. | 31 |
| SEQ ID No. 44 | 75° C. | 70 |
| | 80° C. | 59 |
| | 85° C. | 48 |
| | 90° C. | 25 |
| SEQ ID No. 45 | 75° C. | 72 |
| | 80° C. | 68 |
| | 85° C. | 48 |
| | 90° C. | 30 |

Example 5: Determination of the Pelletizing Stability of *Fusarium* Toxin-Degrading Polypeptides Selected polypeptide variants were cloned in *Pichia pastoris* in a bioreactor using standard methods under controlled aerobic conditions and extracellularly secreted. The clear supernatant was separated from the biomass, supplemented with a carrier substance (maltodextrin) and processed to a pelletizable powder using a spray-dryer. The *fusarium* toxin-degrading polypeptide variants present in power form were admixed to piglet rearing feed, each at the same concentration of 100 U/kg, and processed to feed pellets in a controlled process. During the pelletizing process, the feed was moistened by hot steaming and heated in individual batches at precisely defined temperatures (75 to 95° C. in 5° C. steps). This preparation phase was followed by the pelletizing process proper. The residual activities of the *fusarium* toxin-degrading polypeptide variants contained in the pellets were determined as described in Example 2, non-pelletized feed containing the respective *fusarium* toxin-degrading polypeptide variants serving as 100% controls. The enzyme activity remaining after the pelletizing process is therefore defined as residual activity. The values are indicated in Table 3.

TABLE 3

Pelletizing temperatures and residual activities of fusarium toxin-degrading polypeptides. <LOQ values are below detection limits (level of quantification: <0.15 U/l in the test mixture)

| Enzyme | Pelletizing temperature | Residual activity % |
| --- | --- | --- |
| SEQ ID No. 1 | 75° C. | 15 |
| | 80° C. | <LOQ |
| | 85° C. | <LOQ |
| | 90° C. | <LOQ |
| SEQ ID No. 4 | 75° C. | 57 |
| | 80° C. | 46 |
| | 85° C. | 37 |
| | 90° C. | 14 |
| SEQ ID No. 43 | 75° C. | 78 |
| | 80° C. | 73 |
| | 85° C. | 58 |
| | 90° C. | 31 |
| SEQ ID No. 44 | 75° C. | 70 |
| | 80° C. | 59 |
| | 85° C. | 48 |
| | 90° C. | 25 |
| SEQ ID No. 45 | 75° C. | 72 |
| | 80° C. | 68 |
| | 85° C. | 48 |
| | 90° C. | 30 |

The invention claimed is:
1. A *fusarium* toxin-cleaving polypeptide variant of a *fusarium* toxin carboxylesterase of SEQ ID NO: 46, wherein the polypeptide variant possesses an amino acid sequence truncated by 47 amino acids at the N-terminus, the amino acid sequence sharing at least 90% sequence identity with the amino acid sequence section 48-540 of SEQ ID NO: 46,
wherein the temperature stability (T(50%)) of the polypeptide of SEQ ID No. 46 is determined to be 42° C., the temperature stability (T(50%)) of the polypeptide of SEQ ID NO: 1 is determined to be 45° C. and, the polypeptide variant has a relative increase of temperature stability (T(50%)) compared to the polypeptide of SEQ ID NO: 1;
wherein the amino acid sequence of the polypeptide variant comprises at least one amino acid substitution at a position according to the numbering of SEQ ID NO: 1 selected from the group consisting of position 10, 33, 66, 107, 140, 144, 149, 151, 157, 199, 266, 267, 270, 272, 275, 280, 284, 286, 293, 302, 312, 329, 332, 360, 363, 364, 365, 367, 371, 372, 377, 389, 391, 394, 418, 419, 424, 427, 429, 430, 436, 440, 443, 447, 453, 455, 456, 457, 462, 463, 464, 465, 469, 473, 478, 487 and 490, and that the amino acid substitution at positions 10 and 456 are selected from Q, E, N, H, K and R, at positions 33, 107, 293 and 332 from E, Q, D, K, R and N, at positions 66, 463 and 478 from D, E, K, N, Q and R, at positions 140 and 490 from P, A, S and N, at positions 144 and 367 from I, L, M and V, at positions 149, 270, 312, 329 and 372 from F, Y, W and H, at positions 151 and 453 from D, E, K and R, at positions 157 and 462 from F, H, W and Y, at positions 199, 302, 365 and 464 from I, L, M and V, at positions 266 and 455 and from A, S and T, at positions 267, 394 and 429 from A, N, P and S, at position 272 from H, N, Q and S, at position 275 from A, D, E, G, K, N, Q, R and S, at position 280 from A, D, E, K, N, P, Q, R and S, at position 284 from A, N, P, S, T and V, at position 286 from A, D, E, K, N, P, R and S, at positions 360, 377, 391, 419 and 427 from A, 1, L S, T and V, at positions 363, 443 and 457 from A, S, T and V, at position 364 from H, 1, L, M, N, Q, S and V, at position 371 from A, 1, L, M, S, T and V, at position 389 from I, L, M and V, at positions 418, 430, 447 and 473 from A, G and S, at position 424 from A, D, E, G, K, R and S, at position 436 from A, G, S and T, at position 440 from A, G, S and T, at position 465 from A, G, H, N, Q, S and T, at position 469 from D, E, K and R and/or at position 487 from N, D, Q, H and S;
wherein the amino acid sequence of the polypeptide variant comprises at least two amino acid substitutions at positions according to the numbering of SEQ ID NO: 1, selected from the group consisting of 10, 33, 66, 107, 140, 144, 149, 151, 157, 199, 266, 267, 270, 272, 275, 280, 284, 286, 293, 302, 312, 329, 332, 360, 363, 364, 365, 367, 371, 372, 377, 389, 391, 394, 418, 419, 424, 427, 429, 430, 436, 440, 443, 447, 453, 455, 456, 457, 462, 463, 464, 465, 469, 473, 478, 487 and 490, wherein the at least two amino acid substitutions are selected from the group consisting of 10Q, 66D, 144M, 151R, 199I, 266S, 267P, 272H, 275E, 275A, 280D, 284T, 286P, 286R, 293E, 302I, 360V, 363T, 364H, 364L, 365I, 367H, 371V, 371M, 372F, 377V, 389L, 391V, 394P, 418A, 419V, 424A, 424K, 427V, 429P, 430A, 436A, 436S, 440G, 440S, 443T, 447A, 453R, 455S, 456Q, 457T, 462Y, 463D, 464I, 465H, 465S, 465G, 469K, 473A, 478D, 487N and 490P; and
wherein the amino acid sequence does not include SEQ ID NO: 1.
2. The polypeptide variant according to claim 1, wherein the amino acid substitutions are selected from the group consisting of 10Q, 33E, 66D, 107E, 140P, 144M, 149F, 151R, 157Y, 199I, 266S, 267P, 270F, 272H, 275E, 275A, 280D, 280P, 284T, 284P, 286P, 286R, 293E, 302I, 312F, 329F, 332E, 360V, 363T, 364H, 364L, 365I, 367H, 371V, 371M, 372F, 377V, 389L, 391V, 394P, 418A, 419V, 424A, 424K, 427V, 429P, 430A, 436A, 436S, 440G, 440S, 443T, 447A, 453R, 455S, 456Q, 457T, 462Y, 463D, 464I, 465H, 465S, 465G, 469K, 473A, 478D, 487N and 490P.
3. The polypeptide variant according to claim 1, wherein the polypeptide variant comprises an amino acid substitution on at least one position selected from the group consisting of 66, 199, 302, 377, 394, 424, 430 and 463.
4. The polypeptide variant according to claim 1, wherein at least one of the amino acid substitutions is selected from the group consisting of 66D, 199I, 302I, 377V, 394P, 424A, 430A and 463D.
5. The polypeptide variant according to claim 1, wherein the amino acid sequence of the polypeptide variant comprises combinations of several amino acid substitutions, wherein the combinations of the positions being selected from the group consisting of 66/199/302/394/424/430, 66/199/302/377/394/424/430, 66/199/302/377/394/424/430/463, 66/144/199/302/360/372/377/394/424/430/443/463, 199/302/377/394/424/430/463, 66/199/302/377/394, 66/199/302/364/377/394/424/430/463, 66/199/302/377/394/424/430/463/465, 66/199/302/377/394/424/430/440/463, 66/199/302/377/394/424/430/447/463, 66/199/302/377/394/418/424/430/463, 66/199/302/377/394/424/436/430/463, 66/199/302/364/377/394/424/430/463, 66/199/302/377/394/424/430/463/490, 66/199/302/377/394/424/430/463/469, 66/199/302/377/389/394/424/430/463, 66/199/302/377/394/424/430/463/465, 66/199/302/377/394/424/430/463/464, 66/199/302/377/394/424/430/463/465, 66/199/302/377/394/424/430/440/463, 66/199/302/377/394/424/430/457/463, 66/199/302/377/394/424/430/436/463, 66/199/302/363/3711/377/394/424/430/463, 66/199/302/377/394/424/430/447/453/463, 66/199/302/377/394/424/430/456/462/463, 66/199/302/377/394/419/424/427/430/463, 66/199/302/365/377/394/424/430/463/487 and 66/199/302/371/377/394/424/430/463/487.
6. The polypeptide variant according to claim 5, wherein the amino acid sequence of the polypeptide variant is selected from the group consisting of SEQ ID Nos. 2 to 29.
7. The polypeptide variant according to claim 1, wherein the amino acid sequence of the polypeptide variant comprises combinations of several amino acid substitutions, the combinations of the positions being selected from the group consisting of 66/99/302/364/377/389/394/419/424/427/430/447/463/465/469, 66/199/302/377/389/394/419/424/427/430/447/463/465/469, 66/199/302/363/364/371/377/389/394/419/424/427/430/447/463/464/465/469, 66/199/302/363/371/377/389/394/419/424/427/430/447/463/464/465/469, 66/199/302/364/367/371/377/389/394/418/419/424/427/430/436/440/447/463/464/465/469/490, 66/199/302/367/371/377/389/394/418/419/424/427/430/436/440/447/463/464/465/469/490, 66/199/302/363/367/371/377/394/424/430/463/490, 66/199/302/377/394/418/419/424/427/430/436/440/447/463, 66/199/302/377/389/394/424/430/457/463/464/465/469, 66/199/302/363/371/377/389/394/419/424/427/430/440/447/457/463/464/469/490, 66/199/302/377/394/424/430/463/447/490/469/465, 66/199/302/377/394/424/430/463/490/46/490/469/465/419/427/371/487, 66/199/302/371/377/394/419/424/427/430/447/453/

463/465/469/487/490, 66/199/302/367/371/377/389/394/418/419/424/427/429/430/436/440/447/457/463/464/465/469/490, 66/199/302/371/377/389/394/419/424/427/430/436/447/453/456/462/463/465/469/490/487 and 66/199/302/367/371/377/389/394/418/419/424/427/429/430/436/440/447/453/456/457/462/463/464/465/469/487/490.

8. The polypeptide variant according to claim 7, wherein the amino acid sequence of the polypeptide variant is selected from the group consisting of SEQ ID Nos. 30 to 45.

9. An isolated polynucleotide, wherein the polynucleotide comprises a nucleotide sequence encoding a polypeptide variant according to claim 1.

10. A preparation for prophylaxis and/or treatment of *fusarium* toxin mycotoxicoses, the preparation comprising a polypeptide variant according to claim 1.

11. A method for hydrolytically cleaving at least one *fusarium* toxin, wherein at least one *fusarium* toxin is contacted with at least one polypeptide variant according to claim 1 and that the mixture of the polypeptide variant and the *fusarium* toxin is subjected to a temperature treatment at at least 50° C. and that the mixture is contacted with an amount of moisture sufficient for hydrolytic cleavage either during or after the temperature treatment.

12. The method according to claim 11, wherein the polypeptide variant is mixed with a feed or food product contaminated with at least one *fusarium* toxin, and the temperature treatment is optionally performed during a pelletizing process.

13. The method according to claim 12, wherein the polypeptide variant is added at a concentration range from 5 U to 500 U per kilogram of feed or food product.

14. A *fusarium* toxin-cleaving additive, wherein said additive comprises at least one polypeptide variant according to claim 1 and optionally at least one supplement material.

15. The additive according to claim 14, wherein the supplement material is selected from the group consisting of inert carriers, vitamins, minerals, phytogenic substances, enzymes and other components for detoxifying mycotoxins, the other components optionally selected from mycotoxin-degrading enzymes, in particular aflatoxin oxidases, ergotamine hydrolases, ergotamine amidases, zearalenone esterases, zearalenone lactonases, zearalenone hydrolases, ochratoxin amidases, fumonisin am inotransferases, aminopolyol am inoxidases, deoxynivalenol epoxide hydrolases, deoxynivalenol dehydrogenases, deoxynivalenol oxidases, trichothecene dehydrogenases, trichothecene oxidases; and mycotoxin-degrading microorganisms; and mycotoxin-binding substances, for instance microbial cell walls or inorganic materials such as bentonite.

16. A method for cleaving at least one *fusarium* toxin comprising the step of contacting the additive according to claim 14 with the at least one *fusarium* toxin in pelletized, food or feed products, for pigs, poultry, cattle, horses, fishes or aquaculture.

17. A method for cleaving at least one *fusarium* toxin comprising the step of contacting the additive according to claim 14 with at least one *fusarium* toxin in food or feed products in a process at temperatures of at least 50° C.

18. A method for hydrolytically cleaving at least one *fusarium* toxin, wherein at least one *fusarium* toxin is contacted with at least one additive according to claim 14 and the mixture of the at least one additive and the at least one *fusarium* toxin is subjected to a temperature treatment at at least 50° C. and that the mixture is contacted with an amount of moisture sufficient for hydrolytic cleavage either during or after the temperature treatment.

19. The method according to claim 18, wherein the at least one additive is mixed with a feed or food product contaminated with at least one *fusarium* toxin, and the temperature treatment is optionally performed during a pelletizing process.

20. The method according to claim 19, wherein the polypeptide variant is added at a concentration range from 5 U to 500 U per kilogram of feed or food product.

* * * * *

SEQUENCE LISTING

<160> NUMBER OF SEQ ID NOS: 46

<210> SEQ ID NO 1
<211> LENGTH: 493
<212> TYPE: PRT
<213> ORGANISM: Artificial sequence
<220> FEATURE:
<223> OTHER INFORMATION: Modified from SEQ ID-Nr. 46

<400> SEQUENCE: 1

```
Gln Thr Asp Asp Pro Lys Leu Val Arg His Thr Gln Ser Gly Ala Val
 1               5                  10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
50                      55                  60

Gly Asn Glu Arg Leu Arg Glu Gly Ser Arg Ala Ala Gly Thr Ser Glu
65                      70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Asp Pro Asn Arg Val Thr Val Phe Gly Glu
            180                 185                 190

Ser Ala Gly Ala Ser Ala Leu Gly Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Leu Val Gly
    290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
        355                 360                 365

Ile Glu Leu Leu Ser Ala Ala Phe Ala Lys Trp Arg Thr Pro Leu Trp
    370                 375                 380

Arg Tyr Arg Phe Thr Gly Ile Pro Gly Ala Gly Arg Arg Pro Ala Thr
385                 390                 395                 400

His Gly Asp Glu Ile Pro Tyr Val Phe Ala Asn Leu Gly Pro Ser Ser
                405                 410                 415
```

```
Val Ser Met Phe Gly Ser Leu Glu Gly Gly Ala Gly Ala Ser Asp Ile
            420                 425                 430

Lys Leu Ala Thr Glu Met Ser Ala Ala Trp Val Ser Phe Ala Val His
        435                 440                 445

Gly Val Pro Asp Gln Gly Thr Lys Ser His Trp Pro Arg Phe Glu Arg
    450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 2
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 2

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285
```

Asp Ala Phe Ala Lys Gly Ala Phe Arg Lys Ile Pro Val Ile Val Gly
            290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
            355                 360                 365

Ile Glu Leu Leu Ser Ala Ala Phe Ala Lys Trp Arg Thr Pro Leu Trp
370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Ala Gly Ala Ala Asp Ile
            420                 425                 430

Lys Leu Ala Thr Glu Met Ser Ala Ala Trp Val Ser Phe Ala Val His
            435                 440                 445

Gly Val Pro Asp Gln Gly Thr Lys Ser His Trp Pro Arg Phe Glu Arg
450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 3
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 3

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

```
Tyr Gly Leu Leu Asp Met Leu Ala Ala Phe Lys Trp Val Gln Asn Asn
                165                 170                 175
Ile Arg Glu Phe Gly Gly Asp Pro Asn Arg Val Thr Val Phe Gly Glu
            180                 185                 190
Ser Ala Gly Ala Ser Ala Ile Gly Leu Leu Leu Thr Ser Pro Leu Ser
        195                 200                 205
Glu Ser Ala Phe Asn Gln Ala Ile Leu Gln Ser Pro Gly Leu Ala Arg
    210                 215                 220
Pro Leu Ala Thr Leu Ser Glu Ser Glu Ala Asn Gly Leu Glu Leu Gly
225                 230                 235                 240
Ala Asp Ile Ser Ala Leu Arg Arg Ala Asp Ala Gly Glu Leu Thr Lys
                245                 250                 255
Ile Ala Gln Ser Arg Ile Pro Met Ser Arg Gln Phe Thr Lys Pro Arg
            260                 265                 270
Pro Met Gly Pro Ile Leu Asp Gly Tyr Val Leu Arg Thr Leu Asp Val
        275                 280                 285
Asp Ala Phe Ala Lys Gly Ala Phe Arg Lys Ile Pro Val Ile Val Gly
    290                 295                 300
Gly Asn Ala Asp Glu Gly Arg Ala Phe Thr Asp Arg Leu Pro Val Lys
305                 310                 315                 320
Thr Val Leu Glu Tyr Arg Ala Tyr Leu Thr Glu Gln Phe Gly Asp Glu
                325                 330                 335
Ala Asp Ala Trp Glu Arg Cys Tyr Pro Ala Asn Ser Asp Ala Asp Val
            340                 345                 350
Pro Ala Ala Val Ala Arg Leu Phe Gly Asp Ser Gln Phe Asn Asn Gly
        355                 360                 365
Ile Glu Leu Leu Ser Ala Ala Phe Val Lys Trp Arg Thr Pro Leu Trp
    370                 375                 380
Arg Tyr Arg Phe Thr Gly Ile Pro Gly Pro Gly Arg Arg Pro Ala Thr
385                 390                 395                 400
His Gly Asp Glu Ile Pro Tyr Val Phe Ala Asn Leu Gly Pro Ser Ser
                405                 410                 415
Val Ser Met Phe Gly Ser Leu Ala Gly Gly Ala Gly Ala Ala Asp Ile
            420                 425                 430
Lys Leu Ala Thr Glu Met Ser Ala Ala Trp Val Ser Phe Ala Val His
        435                 440                 445
Gly Val Pro Asp Gln Gly Thr Lys Ser His Trp Pro Arg Phe Glu Arg
    450                 455                 460
Arg Gly Glu Ile Met Thr Phe Gly Ser Gln Val Gly Ser Gly Glu Gly
465                 470                 475                 480
Leu Gly Val Ser Pro Ser Lys Ala Cys Gln Pro Ser Lys
                485                 490
```

<210> SEQ ID NO 4
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 4

```
Gln Thr Asp Asp Pro Lys Leu Val Arg His Thr Gln Ser Gly Ala Val
1               5                   10                  15
Glu Gly Val Glu Gly Asp Val Thr Phe Leu Gly Ile Pro Phe Ala
            20                  25                  30
```

```
Ala Pro Pro Val Gly Asp Leu Arg Trp Arg Pro Ala Pro Pro Arg
         35                  40                  45

Ala Trp Ala Gly Thr Arg Asp Gly Arg Arg Phe Ala Pro Asp Cys Ile
 50                  55                  60

Gly Asp Glu Arg Leu Arg Glu Gly Ser Arg Ala Ala Gly Thr Ser Glu
 65              70                  75                      80

Asp Cys Leu Tyr Leu Asn Ile Trp Ser Pro Lys Gln Val Gly Lys Gly
                 85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
            210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
            355                 360                 365

Ile Glu Leu Leu Ser Ala Ala Phe Val Lys Trp Arg Thr Pro Leu Trp
370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Gly Ala Gly Ala Ala Asp Ile
            420                 425                 430

Lys Leu Ala Thr Glu Met Ser Ala Ala Trp Val Ser Phe Ala Val His
            435                 440                 445

Gly Val Pro Asp Gln Gly Thr Lys Ser His Trp Pro Arg Phe Asp Arg
```

```
              450                 455                 460
Arg Gly Glu Ile Met Thr Phe Gly Ser Gln Val Gly Ser Glu Gly
465                 470                 475                 480

Leu Gly Val Ser Pro Ser Lys Ala Cys Gln Pro Ser Lys
                485                 490

<210> SEQ ID NO 5
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 5

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Met
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
```

```
                        325                 330                 335
Ala Asp Ala Trp Glu Arg Cys Tyr Pro Ala Asn Ser Asp Ala Asp Val
            340                 345                 350

Pro Ala Ala Val Ala Arg Leu Val Gly Asp Ser Gln Phe Asn Asn Gly
            355                 360                 365

Ile Glu Leu Phe Ser Ala Ala Phe Val Lys Trp Arg Thr Pro Leu Trp
            370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Ala Gly Ala Ala Asp Ile
            420                 425                 430

Lys Leu Ala Thr Glu Met Ser Ala Ala Trp Thr Ser Phe Ala Val His
            435                 440                 445

Gly Val Pro Asp Gln Gly Thr Lys Ser His Trp Pro Arg Phe Asp Arg
450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 6
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 6

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Pro Ala Pro Pro Arg
            35                  40                  45

Ala Trp Ala Gly Thr Arg Asp Gly Arg Arg Phe Ala Pro Asp Cys Ile
        50                  55                  60

Gly Asn Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
        130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
```

```
                195                 200                 205
Glu Ser Ala Phe Asn Gln Ala Ile Leu Gln Ser Pro Gly Leu Ala Arg
    210                 215                 220
Pro Leu Ala Thr Leu Ser Glu Ser Glu Ala Asn Gly Leu Glu Leu Gly
225                 230                 235                 240
Ala Asp Ile Ser Ala Leu Arg Arg Ala Asp Ala Gly Glu Leu Thr Lys
                245                 250                 255
Ile Ala Gln Ser Arg Ile Pro Met Ser Arg Gln Phe Thr Lys Pro Arg
            260                 265                 270
Pro Met Gly Pro Ile Leu Asp Gly Tyr Val Leu Arg Thr Leu Asp Val
            275                 280                 285
Asp Ala Phe Ala Lys Gly Ala Phe Arg Lys Ile Pro Val Ile Val Gly
        290                 295                 300
Gly Asn Ala Asp Glu Gly Arg Ala Phe Thr Asp Arg Leu Pro Val Lys
305                 310                 315                 320
Thr Val Leu Glu Tyr Arg Ala Tyr Leu Thr Glu Gln Phe Gly Asp Glu
                325                 330                 335
Ala Asp Ala Trp Glu Arg Cys Tyr Pro Ala Asn Ser Asp Ala Asp Val
            340                 345                 350
Pro Ala Ala Val Ala Arg Leu Phe Gly Asp Ser Gln Phe Asn Asn Gly
            355                 360                 365
Ile Glu Leu Leu Ser Ala Ala Phe Val Lys Trp Arg Thr Pro Leu Trp
        370                 375                 380
Arg Tyr Arg Phe Thr Gly Ile Pro Gly Pro Gly Arg Arg Pro Ala Thr
385                 390                 395                 400
His Gly Asp Glu Ile Pro Tyr Val Phe Ala Asn Leu Gly Pro Ser Ser
                405                 410                 415
Val Ser Met Phe Gly Ser Leu Ala Gly Gly Ala Gly Ala Ala Asp Ile
            420                 425                 430
Lys Leu Ala Thr Glu Met Ser Ala Ala Trp Val Ser Phe Ala Val His
            435                 440                 445
Gly Val Pro Asp Gln Gly Thr Lys Ser His Trp Pro Arg Phe Asp Arg
        450                 455                 460
Arg Gly Glu Ile Met Thr Phe Gly Ser Gln Val Gly Ser Gly Glu Gly
465                 470                 475                 480
Leu Gly Val Ser Pro Ser Lys Ala Cys Gln Pro Ser Lys
                485                 490

<210> SEQ ID NO 7
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 7

Gln Thr Asp Asp Pro Lys Leu Val Arg His Thr Gln Ser Gly Ala Val
1               5                   10                  15
Glu Gly Val Glu Gly Asp Val Glu Thr Phe Leu Gly Ile Pro Phe Ala
            20                  25                  30
Ala Pro Pro Val Gly Asp Leu Arg Trp Arg Pro Pro Ala Pro Pro Arg
        35                  40                  45
Ala Trp Ala Gly Thr Arg Asp Gly Arg Arg Phe Ala Pro Asp Cys Ile
    50                  55                  60
Gly Asp Glu Arg Leu Arg Glu Gly Ser Arg Ala Ala Gly Thr Ser Glu
```

```
                65                  70                  75                  80
Asp Cys Leu Tyr Leu Asn Ile Trp Ser Pro Lys Gln Val Gly Lys Gly
                        85                  90                  95

Gly Leu Pro Val Met Ile Trp Val Tyr Gly Gly Phe Ser Gly Gly
                100                 105                 110

Ser Gly Ala Val Pro Tyr Tyr Asp Gly Ser Ala Leu Ala Gln Lys Gly
            115                 120                 125

Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                    165                 170                 175

Ile Arg Glu Phe Gly Gly Asp Pro Asn Arg Val Thr Val Phe Gly Glu
                180                 185                 190

Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                    245                 250                 255

Ile Ala Gln Ser Arg Ile Pro Met Ser Arg Gln Phe Thr Lys Pro Arg
                260                 265                 270

Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
    290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                    325                 330                 335

Ala Asp Ala Trp Glu Arg Cys Tyr Pro Ala Asn Ser Asp Ala Asp Val
                340                 345                 350

Pro Ala Ala Val Ala Arg Leu Phe Gly Asp Ser Gln Phe Asn Asn Gly
            355                 360                 365

Ile Glu Leu Leu Ser Ala Ala Phe Val Lys Trp Arg Thr Pro Leu Trp
    370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                    405                 410                 415

Val Ser Met Phe Gly Ser Leu Glu Gly Ala Gly Ala Ser Asp Ile
                420                 425                 430

Lys Leu Ala Thr Glu Met Ser Ala Ala Trp Val Ser Phe Ala Val His
            435                 440                 445

Gly Val Pro Asp Gln Gly Thr Lys Ser His Trp Pro Arg Phe Glu Arg
    450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                    485                 490
```

```
<210> SEQ ID NO 8
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 8

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
    290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser His Phe Asn Asn Gly
        355                 360                 365
```

```
Ile Glu Leu Leu Ser Ala Ala Phe Val Lys Trp Arg Thr Pro Leu Trp
    370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Ala Gly Ala Ala Asp Ile
            420                 425                 430

Lys Leu Ala Thr Glu Met Ser Ala Ala Trp Val Ser Phe Ala Val His
        435                 440                 445

Gly Val Pro Asp Gln Gly Thr Lys Ser His Trp Pro Arg Phe Asp Arg
    450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 9
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 9

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Lys Gly
                85                  90                  95

Gly Leu Pro Val Met Ile Trp Val Tyr Gly Gly Gly Phe Ser Gly Gly
                100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240
```

```
Ala Asp Ile Ser Ala Leu Arg Arg Ala Asp Ala Gly Glu Leu Thr Lys
            245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
            290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
            325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
            355                 360                 365

Ile Glu Leu Leu Ser Ala Ala Phe Val Lys Trp Arg Thr Pro Leu Trp
            370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
            405                 410                 415

Val Ser Met Phe Gly Ser Leu Ala Gly Ala Gly Ala Ala Asp Ile
            420                 425                 430

Lys Leu Ala Thr Glu Met Ser Ala Trp Val Ser Phe Ala Val His
            435                 440                 445

Gly Val Pro Asp Gln Gly Thr Lys Ser His Trp Pro Arg Phe Asp Arg
450                 455                 460

His Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
            485                 490

<210> SEQ ID NO 10
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 10

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
            35                  40                  45

Ala Trp Ala Gly Thr Arg Asp Gly Arg Arg Phe Ala Pro Asp Cys Ile
            50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
            85                  90                  95

Gly Leu Pro Val Met Ile Trp Val Tyr Gly Gly Gly Phe Ser Gly Gly
            100                 105                 110
```

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
                180                 185                 190

Ser Ala Gly Ala Ser Ala Ile Gly Leu Leu Thr Ser Pro Leu Ser
        195                 200                 205

Glu Ser Ala Phe Asn Gln Ala Ile Leu Gln Ser Pro Gly Leu Ala Arg
        210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
                260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
        290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
                340                 345                 350

Pro Ala Ala Val Ala Arg Leu Phe Gly Asp Ser Gln Phe Asn Asn Gly
        355                 360                 365

Ile Glu Leu Leu Ser Ala Ala Phe Val Lys Trp Arg Thr Pro Leu Trp
        370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Ala Gly Ala Ala Asp Ile
                420                 425                 430

Lys Leu Ala Thr Glu Met Ser Gly Ala Trp Val Ser Phe Ala Val His
        435                 440                 445

Gly Val Pro Asp Gln Gly Thr Lys Ser His Trp Pro Arg Phe Asp Arg
450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 11
<211> LENGTH: 493
<212> TYPE: PRT
<213> ORGANISM: Artificial sequence
<220> FEATURE:

<223> OTHER INFORMATION: Polypeptidvariante der SEQ ID-Nr. 1

<400> SEQUENCE: 11

```
Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
        130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
        210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
        290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
        355                 360                 365

Ile Glu Leu Leu Ser Ala Ala Phe Val Lys Trp Arg Thr Pro Leu Trp
    370                 375                 380

Arg Tyr Arg Phe Thr Gly Ile Pro Gly Pro Gly Arg Arg Pro Ala Thr
385                 390                 395                 400
```

His Gly Asp Glu Ile Pro Tyr Val Phe Ala Asn Leu Gly Pro Ser Ser
              405                 410                 415

Val Ser Met Phe Gly Ser Leu Ala Gly Ala Gly Ala Ala Asp Ile
        420                 425                 430

Lys Leu Ala Thr Glu Met Ser Ala Ala Trp Val Ser Phe Ala Ala His
            435                 440                 445

Gly Val Pro Asp Gln Gly Thr Lys Ser His Trp Pro Arg Phe Asp Arg
    450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 12
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 12

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

```
Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
        290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
        355                 360                 365

Ile Glu Leu Leu Ser Ala Ala Phe Val Lys Trp Arg Thr Pro Leu Trp
    370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ala Met Phe Gly Ser Leu Ala Gly Gly Ala Gly Ala Ala Asp Ile
            420                 425                 430

Lys Leu Ala Thr Glu Met Ser Ala Ala Trp Val Ser Phe Ala Val His
        435                 440                 445

Gly Val Pro Asp Gln Gly Thr Lys Ser His Trp Pro Arg Phe Asp Arg
    450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 13
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 13

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140
```

```
Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
    290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
        355                 360                 365

Ile Glu Leu Leu Ser Ala Ala Phe Val Lys Trp Arg Thr Pro Leu Trp
    370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Gly Ala Gly Ala Ala Asp Ile
            420                 425                 430

Lys Leu Ala Ala Glu Met Ser Ala Ala Trp Val Ser Phe Ala Val His
        435                 440                 445

Gly Val Pro Asp Gln Gly Thr Lys Ser His Trp Pro Arg Phe Asp Arg
    450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490
```

<210> SEQ ID NO 14
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 14

```
Gln Thr Asp Asp Pro Lys Leu Val Arg His Thr Gln Ser Gly Ala Val
1               5                   10                  15
```

-continued

```
Glu Gly Val Glu Gly Asp Val Glu Thr Phe Leu Gly Ile Pro Phe Ala
             20                  25                  30
Ala Pro Pro Val Gly Asp Leu Arg Trp Arg Pro Ala Pro Pro Arg
         35                  40                  45
Ala Trp Ala Gly Thr Arg Asp Gly Arg Arg Phe Ala Pro Asp Cys Ile
     50                  55                  60
Gly Asp Glu Arg Leu Arg Glu Gly Ser Arg Ala Ala Gly Thr Ser Glu
65                  70                  75                  80
Asp Cys Leu Tyr Leu Asn Ile Trp Ser Pro Lys Gln Val Gly Lys Gly
                 85                  90                  95
Gly Leu Pro Val Met Ile Trp Val Tyr Gly Gly Gly Phe Ser Gly Gly
             100                 105                 110
Ser Gly Ala Val Pro Tyr Tyr Asp Gly Ser Ala Leu Ala Gln Lys Gly
         115                 120                 125
Val Val Val Val Thr Phe Asn Tyr Arg Ala Gly Ile Leu Gly Phe Leu
    130                 135                 140
Ala His Pro Ala Leu Ser Lys Glu Ser Pro Asn Gly Val Ser Gly Asn
145                 150                 155                 160
Tyr Gly Leu Leu Asp Met Leu Ala Ala Phe Lys Trp Val Gln Asn Asn
                 165                 170                 175
Ile Arg Glu Phe Gly Asp Pro Asn Arg Val Thr Val Phe Gly Glu
             180                 185                 190
Ser Ala Gly Ala Ser Ala Ile Gly Leu Leu Leu Thr Ser Pro Leu Ser
         195                 200                 205
Glu Ser Ala Phe Asn Gln Ala Ile Leu Gln Ser Pro Gly Leu Ala Arg
210                 215                 220
Pro Leu Ala Thr Leu Ser Glu Ser Glu Ala Asn Gly Leu Glu Leu Gly
225                 230                 235                 240
Ala Asp Ile Ser Ala Leu Arg Arg Ala Asp Ala Gly Glu Leu Thr Lys
                 245                 250                 255
Ile Ala Gln Ser Arg Ile Pro Met Ser Arg Gln Phe Thr Lys Pro Arg
             260                 265                 270
Pro Met Gly Pro Ile Leu Asp Gly Tyr Val Leu Arg Thr Leu Asp Val
         275                 280                 285
Asp Ala Phe Ala Lys Gly Ala Phe Arg Lys Ile Pro Val Ile Val Gly
    290                 295                 300
Gly Asn Ala Asp Glu Gly Arg Ala Phe Thr Asp Arg Leu Pro Val Lys
305                 310                 315                 320
Thr Val Leu Glu Tyr Arg Ala Tyr Leu Thr Glu Gln Phe Gly Asp Glu
                 325                 330                 335
Ala Asp Ala Trp Glu Arg Cys Tyr Pro Ala Asn Ser Asp Ala Asp Val
             340                 345                 350
Pro Ala Ala Val Ala Arg Leu Phe Gly Asp Ser Leu Phe Asn Asn Gly
         355                 360                 365
Ile Glu Leu Leu Ser Ala Ala Phe Val Lys Trp Arg Thr Pro Leu Trp
    370                 375                 380
Arg Tyr Arg Phe Thr Gly Ile Pro Gly Pro Gly Arg Arg Pro Ala Thr
385                 390                 395                 400
His Gly Asp Glu Ile Pro Tyr Val Phe Ala Asn Leu Gly Pro Ser Ser
                 405                 410                 415
Val Ser Met Phe Gly Ser Leu Ala Gly Gly Ala Gly Ala Ala Asp Ile
             420                 425                 430
Lys Leu Ala Thr Glu Met Ser Ala Ala Trp Val Ser Phe Ala Val His
```

```
              435                 440                 445
Gly Val Pro Asp Gln Gly Thr Lys Ser His Trp Pro Arg Phe Asp Arg
        450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 15
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 15

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
    290                 295                 300

Gly Asn Ala Asp Glu Gly Arg Ala Phe Thr Asp Arg Leu Pro Val Lys
```

```
                    305                 310                 315                 320
            Thr Val Leu Glu Tyr Arg Ala Tyr Leu Thr Glu Gln Phe Gly Asp Glu
                            325                 330                 335

Ala Asp Ala Trp Glu Arg Cys Tyr Pro Ala Asn Ser Asp Ala Asp Val
                            340                 345                 350

Pro Ala Ala Val Ala Arg Leu Phe Gly Asp Ser Gln Phe Asn Asn Gly
                            355                 360                 365

Ile Glu Leu Leu Ser Ala Ala Phe Val Lys Trp Arg Thr Pro Leu Trp
                            370                 375                 380

Arg Tyr Arg Phe Thr Gly Ile Pro Gly Pro Gly Arg Arg Pro Ala Thr
            385                 390                 395                 400

His Gly Asp Glu Ile Pro Tyr Val Phe Ala Asn Leu Gly Pro Ser Ser
                            405                 410                 415

Val Ser Met Phe Gly Ser Leu Ala Gly Gly Ala Gly Ala Ala Asp Ile
                            420                 425                 430

Lys Leu Ala Thr Glu Met Ser Ala Ala Trp Val Ser Phe Ala Val His
                            435                 440                 445

Gly Val Pro Asp Gln Gly Thr Lys Ser His Trp Pro Arg Phe Asp Arg
                            450                 455                 460

Arg Gly Glu Ile Met Thr Phe Gly Ser Gln Val Gly Ser Gly Glu Gly
            465                 470                 475                 480

Leu Gly Val Ser Pro Ser Lys Ala Cys Pro Pro Ser Lys
                            485                 490

<210> SEQ ID NO 16
            <211> LENGTH: 493
            <212> TYPE: PRT
            <213> ORGANISM: Artificial sequence
            <220> FEATURE:
            <223> OTHER INFORMATION: Polypeptidvariante der SEQ ID-Nr. 1

<400> SEQUENCE: 16

Gln Thr Asp Asp Pro Lys Leu Val Arg His Thr Gln Ser Gly Ala Val
            1               5                   10                  15

Glu Gly Val Glu Gly Asp Val Glu Thr Phe Leu Gly Ile Pro Phe Ala
                            20                  25                  30

Ala Pro Pro Val Gly Asp Leu Arg Trp Arg Pro Pro Ala Pro Pro Arg
                            35                  40                  45

Ala Trp Ala Gly Thr Arg Asp Gly Arg Arg Phe Ala Pro Asp Cys Ile
                            50                  55                  60

Gly Asp Glu Arg Leu Arg Glu Gly Ser Arg Ala Ala Gly Thr Ser Glu
            65                  70                  75                  80

Asp Cys Leu Tyr Leu Asn Ile Trp Ser Pro Lys Gln Val Gly Lys Gly
                            85                  90                  95

Gly Leu Pro Val Met Ile Trp Val Tyr Gly Gly Phe Ser Gly Gly
                            100                 105                 110

Ser Gly Ala Val Pro Tyr Tyr Asp Gly Ser Ala Leu Ala Gln Lys Gly
                            115                 120                 125

Val Val Val Val Thr Phe Asn Tyr Arg Ala Gly Ile Leu Gly Phe Leu
                            130                 135                 140

Ala His Pro Ala Leu Ser Lys Glu Ser Pro Asn Gly Val Ser Gly Asn
            145                 150                 155                 160

Tyr Gly Leu Leu Asp Met Leu Ala Ala Phe Lys Trp Val Gln Asn Asn
                            165                 170                 175

Ile Arg Glu Phe Gly Gly Asp Pro Asn Arg Val Thr Val Phe Gly Glu
```

```
            180                 185                 190
Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
        210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
    290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
        355                 360                 365

Ile Glu Leu Leu Ser Ala Ala Phe Val Lys Trp Arg Thr Pro Leu Trp
    370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Gly Ala Gly Ala Ala Asp Ile
            420                 425                 430

Lys Leu Ala Thr Glu Met Ser Ala Ala Trp Val Ser Phe Ala Val His
        435                 440                 445

Gly Val Pro Asp Gln Gly Thr Lys Ser His Trp Pro Arg Phe Asp Arg
    450                 455                 460

Arg Gly Glu Ile Lys Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 17
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 17

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
                20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
```

```
              50                  55                  60
Gly Asp Glu Arg Leu Arg Glu Gly Ser Arg Ala Ala Gly Thr Ser Glu
 65                  70                  75                  80

Asp Cys Leu Tyr Leu Asn Ile Trp Ser Pro Lys Gln Val Gly Lys Gly
                 85                  90                  95

Gly Leu Pro Val Met Ile Trp Val Tyr Gly Gly Phe Ser Gly Gly
                100                 105                 110

Ser Gly Ala Val Pro Tyr Tyr Asp Gly Ser Ala Leu Ala Gln Lys Gly
                115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
                180                 185                 190

Ser Ala Gly Ala Ser Ala Ile Gly Leu Leu Leu Thr Ser Pro Leu Ser
                195                 200                 205

Glu Ser Ala Phe Asn Gln Ala Ile Leu Gln Ser Pro Gly Leu Ala Arg
                210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
                260                 265                 270

Pro Met Gly Pro Ile Leu Asp Gly Tyr Val Leu Arg Thr Leu Asp Val
                275                 280                 285

Asp Ala Phe Ala Lys Gly Ala Phe Arg Lys Ile Pro Val Ile Val Gly
                290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
                340                 345                 350

Pro Ala Ala Val Ala Arg Leu Phe Gly Asp Ser Gln Phe Asn Asn Gly
                355                 360                 365

Ile Glu Leu Leu Ser Ala Ala Phe Val Lys Trp Arg Thr Pro Leu Trp
                370                 375                 380

Arg Tyr Arg Phe Leu Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Gly Ala Gly Ala Ala Asp Ile
                420                 425                 430

Lys Leu Ala Thr Glu Met Ser Ala Ala Trp Val Ser Phe Ala Val His
                435                 440                 445

Gly Val Pro Asp Gln Gly Thr Lys Ser His Trp Pro Arg Phe Asp Arg
                450                 455                 460

Arg Gly Glu Ile Met Thr Phe Gly Ser Gln Val Gly Ser Gly Glu Gly
465                 470                 475                 480
```

```
Leu Gly Val Ser Pro Ser Lys Ala Cys Gln Pro Ser Lys
            485                 490
```

<210> SEQ ID NO 18
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 18

```
Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
    290                 295                 300

Gly Asn Ala Asp Glu Gly Arg Ala Phe Thr Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350
```

```
Pro Ala Ala Val Ala Arg Leu Phe Gly Asp Ser Gln Phe Asn Asn Gly
        355                 360                 365

Ile Glu Leu Leu Ser Ala Ala Phe Val Lys Trp Arg Thr Pro Leu Trp
    370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Ala Gly Ala Ala Asp Ile
            420                 425                 430

Lys Leu Ala Thr Glu Met Ser Ala Ala Trp Val Ser Phe Ala Val His
        435                 440                 445

Gly Val Pro Asp Gln Gly Thr Lys Ser His Trp Pro Arg Phe Asp Arg
    450                 455                 460

Ser Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 19
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 19

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220
```

```
Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
            245                 250                 255

Ile Ala Gln Ser Arg Ile Pro Met Ser Arg Gln Phe Thr Lys Pro Arg
        260                 265                 270

Pro Met Gly Pro Ile Leu Asp Gly Tyr Val Leu Arg Thr Leu Asp Val
    275                 280                 285

Asp Ala Phe Ala Lys Gly Ala Phe Arg Lys Ile Pro Val Ile Val Gly
290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
            325                 330                 335

Ala Asp Ala Trp Glu Arg Cys Tyr Pro Ala Asn Ser Asp Ala Asp Val
        340                 345                 350

Pro Ala Ala Val Ala Arg Leu Phe Gly Asp Ser Gln Phe Asn Asn Gly
    355                 360                 365

Ile Glu Leu Leu Ser Ala Ala Phe Val Lys Trp Arg Thr Pro Leu Trp
370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
            405                 410                 415

Val Ser Met Phe Gly Ser Leu Ala Gly Ala Gly Ala Ala Asp Ile
        420                 425                 430

Lys Leu Ala Thr Glu Met Ser Ala Ala Trp Val Ser Phe Ala Val His
    435                 440                 445

Gly Val Pro Asp Gln Gly Thr Lys Ser His Trp Pro Arg Phe Asp Ile
450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
            485                 490

<210> SEQ ID NO 20
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 20

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
            85                  90                  95
```

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
            210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
            290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
            355                 360                 365

Ile Glu Leu Leu Ser Ala Ala Phe Val Lys Trp Arg Thr Pro Leu Trp
370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Gly Ala Gly Ala Ala Asp Ile
            420                 425                 430

Lys Leu Ala Thr Glu Met Ser Ala Ala Trp Val Ser Phe Ala Val His
            435                 440                 445

Gly Val Pro Asp Gln Gly Thr Lys Ser His Trp Pro Arg Phe Asp Arg
            450                 455                 460

Gly Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 21
<211> LENGTH: 493

<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 21

```
Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
            35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
    290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
            355                 360                 365

Ile Glu Leu Leu Ser Ala Ala Phe Val Lys Trp Arg Thr Pro Leu Trp
    370                 375                 380
```

```
Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
            405                 410                 415

Val Ser Met Phe Gly Ser Leu Ala Gly Ala Gly Ala Ala Asp Ile
        420                 425                 430

Lys Leu Ala Thr Glu Met Ser Ser Ala Trp Val Ser Phe Ala Val His
            435                 440                 445

Gly Val Pro Asp Gln Gly Thr Lys Ser His Trp Pro Arg Phe Asp Arg
        450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 22
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 22

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Pro Pro Arg
        35                  40                  45

Ala Trp Ala Gly Thr Arg Asp Gly Arg Arg Phe Ala Pro Asp Cys Ile
50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Lys Gly
            85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
        130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255
```

Ile Ala Gln Ser Arg Ile Pro Met Ser Arg Gln Phe Thr Lys Pro Arg
             260                 265                 270

Pro Met Gly Pro Ile Leu Asp Gly Tyr Val Leu Arg Thr Leu Asp Val
         275                 280                 285

Asp Ala Phe Ala Lys Gly Ala Phe Arg Lys Ile Pro Val Ile Val Gly
     290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
             325                 330                 335

Ala Asp Ala Trp Glu Arg Cys Tyr Pro Ala Asn Ser Asp Ala Asp Val
         340                 345                 350

Pro Ala Ala Val Ala Arg Leu Phe Gly Asp Ser Gln Phe Asn Asn Gly
     355                 360                 365

Ile Glu Leu Leu Ser Ala Ala Phe Val Lys Trp Arg Thr Pro Leu Trp
370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
             405                 410                 415

Val Ser Met Phe Gly Ser Leu Ala Gly Ala Gly Ala Ala Asp Ile
         420                 425                 430

Lys Leu Ala Thr Glu Met Ser Ala Ala Trp Val Ser Phe Ala Val His
     435                 440                 445

Gly Val Pro Asp Gln Gly Thr Lys Thr His Trp Pro Arg Phe Asp Arg
450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
             485                 490

<210> SEQ ID NO 23
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 23

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
             20                  25                  30

Ala Pro Pro Val Gly Asp Leu Arg Trp Arg Pro Pro Ala Pro Pro Arg
         35                  40                  45

Ala Trp Ala Gly Thr Arg Asp Gly Arg Arg Phe Ala Pro Asp Cys Ile
     50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
             85                  90                  95

Gly Leu Pro Val Met Ile Trp Val Tyr Gly Gly Phe Ser Gly Gly
         100                 105                 110

Ser Gly Ala Val Pro Tyr Tyr Asp Gly Ser Ala Leu Ala Gln Lys Gly
     115                 120                 125

Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Thr Ser Pro Leu Ser
        195                 200                 205

Glu Ser Ala Phe Asn Gln Ala Ile Leu Gln Ser Pro Gly Leu Ala Arg
210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
        355                 360                 365

Ile Glu Leu Leu Ser Ala Ala Phe Val Lys Trp Arg Thr Pro Leu Trp
370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Gly Ala Gly Ala Ala Asp Ile
            420                 425                 430

Lys Leu Ala Ser Glu Met Ser Ala Ala Trp Val Ser Phe Ala Val His
        435                 440                 445

Gly Val Pro Asp Gln Gly Thr Lys Ser His Trp Pro Arg Phe Asp Arg
450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 24
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 24

-continued

```
Gln Thr Asp Asp Pro Lys Leu Val Arg His Thr Gln Ser Gly Ala Val
1               5                   10                  15
Glu Gly Val Glu Gly Asp Val Glu Thr Phe Leu Gly Ile Pro Phe Ala
            20                  25                  30
Ala Pro Pro Val Gly Asp Leu Arg Trp Arg Pro Ala Pro Pro Arg
        35                  40                  45
Ala Trp Ala Gly Thr Arg Asp Gly Arg Arg Phe Ala Pro Asp Cys Ile
    50                  55                  60
Gly Asp Glu Arg Leu Arg Glu Gly Ser Arg Ala Ala Gly Thr Ser Glu
65                  70                  75                  80
Asp Cys Leu Tyr Leu Asn Ile Trp Ser Pro Lys Gln Val Gly Lys Gly
                85                  90                  95
Gly Leu Pro Val Met Ile Trp Val Tyr Gly Gly Phe Ser Gly Gly
            100                 105                 110
Ser Gly Ala Val Pro Tyr Tyr Asp Gly Ser Ala Leu Ala Gln Lys Gly
        115                 120                 125
Val Val Val Val Thr Phe Asn Tyr Arg Ala Gly Ile Leu Gly Phe Leu
    130                 135                 140
Ala His Pro Ala Leu Ser Lys Glu Ser Pro Asn Gly Val Ser Gly Asn
145                 150                 155                 160
Tyr Gly Leu Leu Asp Met Leu Ala Ala Phe Lys Trp Val Gln Asn Asn
                165                 170                 175
Ile Arg Glu Phe Gly Gly Asp Pro Asn Arg Val Thr Val Phe Gly Glu
            180                 185                 190
Ser Ala Gly Ala Ser Ala Ile Gly Leu Leu Thr Ser Pro Leu Ser
        195                 200                 205
Glu Ser Ala Phe Asn Gln Ala Ile Leu Gln Ser Pro Gly Leu Ala Arg
    210                 215                 220
Pro Leu Ala Thr Leu Ser Glu Ser Glu Ala Asn Gly Leu Glu Leu Gly
225                 230                 235                 240
Ala Asp Ile Ser Ala Leu Arg Arg Ala Asp Ala Gly Glu Leu Thr Lys
                245                 250                 255
Ile Ala Gln Ser Arg Ile Pro Met Ser Arg Gln Phe Thr Lys Pro Arg
            260                 265                 270
Pro Met Gly Pro Ile Leu Asp Gly Tyr Val Leu Arg Thr Leu Asp Val
        275                 280                 285
Asp Ala Phe Ala Lys Gly Ala Phe Arg Lys Ile Pro Val Ile Val Gly
    290                 295                 300
Gly Asn Ala Asp Glu Gly Arg Ala Phe Thr Asp Arg Leu Pro Val Lys
305                 310                 315                 320
Thr Val Leu Glu Tyr Arg Ala Tyr Leu Thr Glu Gln Phe Gly Asp Glu
                325                 330                 335
Ala Asp Ala Trp Glu Arg Cys Tyr Pro Ala Asn Ser Asp Ala Asp Val
            340                 345                 350
Pro Ala Ala Val Ala Arg Leu Phe Gly Asp Thr Gln Phe Asn Asn Gly
        355                 360                 365
Ile Glu Val Leu Ser Ala Ala Phe Val Lys Trp Arg Thr Pro Leu Trp
    370                 375                 380
Arg Tyr Arg Phe Thr Gly Ile Pro Gly Pro Gly Arg Arg Pro Ala Thr
385                 390                 395                 400
His Gly Asp Glu Ile Pro Tyr Val Phe Ala Asn Leu Gly Pro Ser Ser
                405                 410                 415
Val Ser Met Phe Gly Ser Leu Ala Gly Gly Ala Gly Ala Ala Asp Ile
```

```
            420             425             430
Lys Leu Ala Thr Glu Met Ser Ala Ala Trp Val Ser Phe Ala Val His
        435             440             445

Gly Val Pro Asp Gln Gly Thr Lys Ser His Trp Pro Arg Phe Asp Arg
    450             455             460

Arg Gly Glu Ile Met Thr Phe Gly Ser Gln Val Gly Ser Gly Glu Gly
465             470             475             480

Leu Gly Val Ser Pro Ser Lys Ala Cys Gln Pro Ser Lys
            485             490

<210> SEQ ID NO 25
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 25

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65              70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
        130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
```

```
              290                 295                 300
Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
                340                 345                 350

Pro Ala Ala Val Ala Arg Leu Phe Gly Asp Ser Gln Phe Asn Asn Gly
            355                 360                 365

Ile Glu Leu Leu Ser Ala Ala Phe Val Lys Trp Arg Thr Pro Leu Trp
370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Gly Ala Gly Ala Ala Asp Ile
                420                 425                 430

Lys Leu Ala Thr Glu Met Ser Ala Ala Trp Val Ser Phe Ala Ala His
            435                 440                 445

Gly Val Pro Asp Arg Gly Thr Lys Ser His Trp Pro Arg Phe Asp Arg
450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 26
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 26

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
                20                  25                  30

Ala Pro Pro Val Gly Asp Leu Arg Trp Arg Pro Ala Pro Pro Arg
            35                  40                  45

Ala Trp Ala Gly Thr Arg Asp Gly Arg Arg Phe Ala Pro Asp Cys Ile
50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
                100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
            130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
```

```
            165                 170                 175
Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
            210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
                260                 265                 270

Pro Met Gly Pro Ile Leu Asp Gly Tyr Val Leu Arg Thr Leu Asp Val
                275                 280                 285

Asp Ala Phe Ala Lys Gly Ala Phe Arg Lys Ile Pro Val Ile Val Gly
            290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
                340                 345                 350

Pro Ala Ala Val Ala Arg Leu Phe Gly Asp Ser Gln Phe Asn Asn Gly
            355                 360                 365

Ile Glu Leu Leu Ser Ala Ala Phe Val Lys Trp Arg Thr Pro Leu Trp
370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Gly Ala Gly Ala Ala Asp Ile
            420                 425                 430

Lys Leu Ala Thr Glu Met Ser Ala Ala Trp Val Ser Phe Ala Val His
            435                 440                 445

Gly Val Pro Asp Gln Gly Thr Gln Ser His Trp Pro Arg Tyr Asp Arg
450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490
```

<210> SEQ ID NO 27
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 27

```
Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Pro Ala Pro Pro Arg
```

```
            35                  40                  45
Ala Trp Ala Gly Thr Arg Asp Gly Arg Arg Phe Ala Pro Asp Cys Ile
 50                  55                  60
Gly Asp Glu Arg Leu Arg Glu Gly Ser Arg Ala Ala Gly Thr Ser Glu
 65                  70                  75                  80
Asp Cys Leu Tyr Leu Asn Ile Trp Ser Pro Lys Gln Val Gly Lys Gly
                 85                  90                  95
Gly Leu Pro Val Met Ile Trp Val Tyr Gly Gly Phe Ser Gly Gly
                100                 105                 110
Ser Gly Ala Val Pro Tyr Tyr Asp Gly Ser Ala Leu Ala Gln Lys Gly
                115                 120                 125
Val Val Val Thr Phe Asn Tyr Arg Ala Gly Ile Leu Gly Phe Leu
                130                 135                 140
Ala His Pro Ala Leu Ser Lys Glu Ser Pro Asn Gly Val Ser Gly Asn
145                 150                 155                 160
Tyr Gly Leu Leu Asp Met Leu Ala Ala Phe Lys Trp Val Gln Asn Asn
                165                 170                 175
Ile Arg Glu Phe Gly Asp Pro Asn Arg Val Thr Val Phe Gly Glu
                180                 185                 190
Ser Ala Gly Ala Ser Ala Ile Gly Leu Leu Leu Thr Ser Pro Leu Ser
                195                 200                 205
Glu Ser Ala Phe Asn Gln Ala Ile Leu Gln Ser Pro Gly Leu Ala Arg
                210                 215                 220
Pro Leu Ala Thr Leu Ser Glu Ser Glu Ala Asn Gly Leu Glu Leu Gly
225                 230                 235                 240
Ala Asp Ile Ser Ala Leu Arg Arg Ala Asp Ala Gly Glu Leu Thr Lys
                245                 250                 255
Ile Ala Gln Ser Arg Ile Pro Met Ser Arg Gln Phe Thr Lys Pro Arg
                260                 265                 270
Pro Met Gly Pro Ile Leu Asp Gly Tyr Val Leu Arg Thr Leu Asp Val
                275                 280                 285
Asp Ala Phe Ala Lys Gly Ala Phe Arg Lys Ile Pro Val Ile Val Gly
                290                 295                 300
Gly Asn Ala Asp Glu Gly Arg Ala Phe Thr Asp Arg Leu Pro Val Lys
305                 310                 315                 320
Thr Val Leu Glu Tyr Arg Ala Tyr Leu Thr Glu Gln Phe Gly Asp Glu
                325                 330                 335
Ala Asp Ala Trp Glu Arg Cys Tyr Pro Ala Asn Ser Asp Ala Asp Val
                340                 345                 350
Pro Ala Ala Val Ala Arg Leu Phe Gly Asp Ser Gln Phe Asn Asn Gly
                355                 360                 365
Ile Glu Leu Leu Ser Ala Ala Phe Val Lys Trp Arg Thr Pro Leu Trp
                370                 375                 380
Arg Tyr Arg Phe Thr Gly Ile Pro Gly Pro Gly Arg Arg Pro Ala Thr
385                 390                 395                 400
His Gly Asp Glu Ile Pro Tyr Val Phe Ala Asn Leu Gly Pro Ser Ser
                405                 410                 415
Val Ser Val Phe Gly Ser Leu Ala Gly Val Gly Ala Ala Asp Ile
                420                 425                 430
Lys Leu Ala Thr Glu Met Ser Ala Ala Trp Val Ser Phe Ala Val His
                435                 440                 445
Gly Val Pro Asp Gln Gly Thr Lys Ser His Trp Pro Arg Phe Asp Arg
                450                 455                 460
```

```
Arg Gly Glu Ile Met Thr Phe Gly Ser Gln Val Ser Gly Glu Gly
465                 470                 475                 480

Leu Gly Val Ser Pro Ser Lys Ala Cys Gln Pro Ser Lys
                485                 490
```

<210> SEQ ID NO 28
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 28

```
Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
                20                  25                  30

Ala Pro Pro Val Gly Asp Leu Arg Trp Arg Pro Ala Pro Pro Arg
            35                  40                  45

Ala Trp Ala Gly Thr Arg Asp Gly Arg Arg Phe Ala Pro Asp Cys Ile
50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
    290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335
```

```
Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Ile Asn Asn Gly
            355                 360                 365

Ile Glu Leu Leu Ser Ala Ala Phe Val Lys Trp Arg Thr Pro Leu Trp
            370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
            405                 410                 415

Val Ser Met Phe Gly Ser Leu Ala Gly Ala Gly Ala Ala Asp Ile
            420                 425                 430

Lys Leu Ala Thr Glu Met Ser Ala Ala Trp Val Ser Phe Ala Val His
            435                 440                 445

Gly Val Pro Asp Gln Gly Thr Lys Ser His Trp Pro Arg Phe Asp Arg
            450                 455                 460

Arg Gly Glu Ile Met Thr Phe Gly Ser Gln Val Gly Ser Gly Glu Gly
465                 470                 475                 480

Leu Gly Val Ser Pro Ser Asn Ala Cys Gln Pro Ser Lys
            485                 490

<210> SEQ ID NO 29
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 29

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
            35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
            130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Thr Ser Pro Leu Ser
            195                 200                 205
```

```
Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
            245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
    290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
        355                 360                 365

Ile Glu Met Leu Ser Ala Ala Phe Val Lys Trp Arg Thr Pro Leu Trp
    370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Gly Ala Gly Ala Ala Asp Ile
            420                 425                 430

Lys Leu Ala Thr Glu Met Ser Ala Ala Trp Val Ser Phe Ala Val His
        435                 440                 445

Gly Val Pro Asp Gln Gly Thr Lys Ser His Trp Pro Arg Phe Asp Arg
    450                 455                 460

Arg Gly Glu Ile Met Thr Phe Gly Ser Gln Val Gly Ser Gly Glu Gly
465                 470                 475                 480

Leu Gly Val Ser Pro Ser Asn Ala Cys Gln Pro Ser Lys
                485                 490

<210> SEQ ID NO 30
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 30

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80
```

```
Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Leu Phe Asn Asn Gly
        355                 360                 365

Ile Glu Leu Leu Ser Ala Ala Phe Val Lys Trp Arg Thr Pro Leu Trp
370                 375                 380

Arg Tyr Arg Phe Leu Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Val Phe Gly Ser Leu Ala Gly Val Gly Ala Ala Asp Ile
            420                 425                 430

Lys Leu Ala Thr Glu Met Ser Ala Ala Trp Val Ser Phe Ala Ala His
        435                 440                 445

Gly Val Pro Asp Gln Gly Thr Lys Ser His Trp Pro Arg Phe Asp Arg
450                 455                 460

Ser Gly Glu Ile Lys Thr Phe Gly Ser Gln Val Gly Ser Gly Glu Gly
465                 470                 475                 480

Leu Gly Val Ser Pro Ser Lys Ala Cys Gln Pro Ser Lys
                485                 490
```

<210> SEQ ID NO 31
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 31

```
Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
    290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
        355                 360                 365
```

-continued

```
Ile Glu Leu Leu Ser Ala Ala Phe Val Lys Trp Arg Thr Pro Leu Trp
370                 375                 380

Arg Tyr Arg Phe Leu Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Val Phe Gly Ser Leu Ala Gly Val Gly Ala Ala Asp Ile
                420                 425                 430

Lys Leu Ala Thr Glu Met Ser Ala Ala Trp Val Ser Phe Ala Ala His
                435                 440                 445

Gly Val Pro Asp Gln Gly Thr Lys Ser His Trp Pro Arg Phe Asp Arg
450                 455                 460

Ser Gly Glu Ile Lys Thr Phe Gly Ser Gln Val Gly Ser Gly Glu Gly
465                 470                 475                 480

Leu Gly Val Ser Pro Ser Lys Ala Cys Gln Pro Ser Lys
                485                 490
```

<210> SEQ ID NO 32
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 32

```
Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
                20                  25                  30

Ala Pro Pro Val Gly Asp Leu Arg Trp Arg Pro Ala Pro Pro Arg
                35                  40                  45

Ala Trp Ala Gly Thr Arg Asp Gly Arg Arg Phe Ala Pro Asp Cys Ile
50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
                100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
                180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240
```

Ala Asp Ile Ser Ala Leu Arg Arg Ala Asp Ala Gly Glu Leu Thr Lys
            245                 250                 255

Ile Ala Gln Ser Arg Ile Pro Met Ser Arg Gln Phe Thr Lys Pro Arg
        260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
            325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Thr Leu Phe Asn Asn Gly
        355                 360                 365

Ile Glu Val Leu Ser Ala Ala Phe Val Lys Trp Arg Thr Pro Leu Trp
        370                 375                 380

Arg Tyr Arg Phe Leu Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
            405                 410                 415

Val Ser Val Phe Gly Ser Leu Ala Gly Val Gly Ala Ala Asp Ile
            420                 425                 430

Lys Leu Ala Thr Glu Met Ser Ala Ala Trp Val Ser Phe Ala Ala His
        435                 440                 445

Gly Val Pro Asp Gln Gly Thr Lys Ser His Trp Pro Arg Phe Asp Ile
    450                 455                 460

Ser Gly Glu Ile Lys Thr Phe Gly Ser Gln Val Gly Ser Gly Glu Gly
465                 470                 475                 480

Leu Gly Val Ser Pro Ser Lys Ala Cys Gln Pro Ser Lys
            485                 490

<210> SEQ ID NO 33
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 33

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
            85                  90                  95

Gly Leu Pro Val Met Ile Trp Val Tyr Gly Gly Gly Phe Ser Gly Gly
            100                 105                 110

```
Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Thr Ser Pro Leu Ser
        195                 200                 205

Glu Ser Ala Phe Asn Gln Ala Ile Leu Gln Ser Pro Gly Leu Ala Arg
210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
        290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Thr Gln Phe Asn Asn Gly
        355                 360                 365

Ile Glu Val Leu Ser Ala Ala Phe Val Lys Trp Arg Thr Pro Leu Trp
370                 375                 380

Arg Tyr Arg Phe Leu Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Val Phe Gly Ser Leu Ala Gly Val Gly Ala Ala Asp Ile
            420                 425                 430

Lys Leu Ala Thr Glu Met Ser Ala Ala Trp Val Ser Phe Ala Ala His
        435                 440                 445

Gly Val Pro Asp Gln Gly Thr Lys Ser His Trp Pro Arg Phe Asp Ile
        450                 455                 460

Ser Gly Glu Ile Lys Thr Phe Gly Ser Gln Val Gly Ser Gly Glu Gly
465                 470                 475                 480

Leu Gly Val Ser Pro Ser Lys Ala Cys Gln Pro Ser Lys
                485                 490
```

<210> SEQ ID NO 34
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 34

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
            210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Leu Phe Asn His Gly
            355                 360                 365

Ile Glu Val Leu Ser Ala Ala Phe Val Lys Trp Arg Thr Pro Leu Trp
            370                 375                 380

Arg Tyr Arg Phe Leu Gly Ile Pro Gly Pro Gly Arg Pro Ala Thr
385                 390                 395                 400

His Gly Asp Glu Ile Pro Tyr Val Phe Ala Asn Leu Gly Pro Ser Ser

```
                        405                 410                 415
Val Ala Val Phe Gly Ser Leu Ala Gly Gly Val Gly Ala Ala Asp Ile
                420                 425                 430

Lys Leu Ala Ala Glu Met Ser Ser Ala Trp Val Ser Phe Ala Ala His
            435                 440                 445

Gly Val Pro Asp Gln Gly Thr Lys Ser His Trp Pro Arg Phe Asp Ile
        450                 455                 460

Ser Gly Glu Ile Lys Thr Phe Gly Ser Gln Val Gly Ser Gly Glu Gly
465                 470                 475                 480

Leu Gly Val Ser Pro Ser Lys Ala Cys Pro Pro Ser Lys
                485                 490

<210> SEQ ID NO 35
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 35

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
```

```
            275                 280                 285
Asp Ala Phe Ala Lys Gly Ala Phe Arg Lys Ile Pro Val Ile Val Gly
        290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn His Gly
        355                 360                 365

Ile Glu Val Leu Ser Ala Ala Phe Val Lys Trp Arg Thr Pro Leu Trp
370                 375                 380

Arg Tyr Arg Phe Leu Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ala Val Phe Gly Ser Leu Ala Gly Val Gly Ala Ala Asp Ile
            420                 425                 430

Lys Leu Ala Ala Glu Met Ser Ser Ala Trp Val Ser Phe Ala Ala His
        435                 440                 445

Gly Val Pro Asp Gln Gly Thr Lys Ser His Trp Pro Arg Phe Asp Ile
450                 455                 460

Ser Gly Glu Ile Lys Thr Phe Gly Ser Gln Val Gly Ser Gly Glu Gly
465                 470                 475                 480

Leu Gly Val Ser Pro Ser Lys Ala Cys Pro Ser Lys
                485                 490

<210> SEQ ID NO 36
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 36

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
```

```
                145                 150                 155                 160
        Tyr Gly Leu Leu Asp Met Leu Ala Ala Phe Lys Trp Val Gln Asn Asn
                        165                 170                 175

Ile Arg Glu Phe Gly Gly Asp Pro Asn Arg Val Thr Val Phe Gly Glu
                        180                 185                 190

Ser Ala Gly Ala Ser Ala Ile Gly Leu Leu Leu Thr Ser Pro Leu Ser
                        195                 200                 205

Glu Ser Ala Phe Asn Gln Ala Ile Leu Gln Ser Pro Gly Leu Ala Arg
                        210                 215                 220

Pro Leu Ala Thr Leu Ser Glu Ser Glu Ala Asn Gly Leu Glu Leu Gly
        225                 230                 235                 240

Ala Asp Ile Ser Ala Leu Arg Arg Ala Asp Ala Gly Glu Leu Thr Lys
                        245                 250                 255

Ile Ala Gln Ser Arg Ile Pro Met Ser Arg Gln Phe Thr Lys Pro Arg
                        260                 265                 270

Pro Met Gly Pro Ile Leu Asp Gly Tyr Val Leu Arg Thr Leu Asp Val
                        275                 280                 285

Asp Ala Phe Ala Lys Gly Ala Phe Arg Lys Ile Pro Val Ile Val Gly
                        290                 295                 300

Gly Asn Ala Asp Glu Gly Arg Ala Phe Thr Asp Arg Leu Pro Val Lys
        305                 310                 315                 320

Thr Val Leu Glu Tyr Arg Ala Tyr Leu Thr Glu Gln Phe Gly Asp Glu
                        325                 330                 335

Ala Asp Ala Trp Glu Arg Cys Tyr Pro Ala Asn Ser Asp Ala Asp Val
                        340                 345                 350

Pro Ala Ala Val Ala Arg Leu Phe Gly Asp Thr Gln Phe Asn His Gly
                        355                 360                 365

Ile Glu Val Leu Ser Ala Ala Phe Val Lys Trp Arg Thr Pro Leu Trp
                        370                 375                 380

Arg Tyr Arg Phe Thr Gly Ile Pro Gly Pro Gly Arg Arg Pro Ala Thr
        385                 390                 395                 400

His Gly Asp Glu Ile Pro Tyr Val Phe Ala Asn Leu Gly Pro Ser Ser
                        405                 410                 415

Val Ser Met Phe Gly Ser Leu Ala Gly Gly Ala Gly Ala Ala Asp Ile
                        420                 425                 430

Lys Leu Ala Thr Glu Met Ser Ala Ala Trp Val Ser Phe Ala Val His
                        435                 440                 445

Gly Val Pro Asp Gln Gly Thr Lys Ser His Trp Pro Arg Phe Asp Arg
        450                 455                 460

Arg Gly Glu Ile Met Thr Phe Gly Ser Gln Val Gly Ser Gly Glu Gly
        465                 470                 475                 480

Leu Gly Val Ser Pro Ser Lys Ala Cys Pro Pro Ser Lys
                        485                 490

<210> SEQ ID NO 37
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 37

Gln Thr Asp Asp Pro Lys Leu Val Arg His Thr Gln Ser Gly Ala Val
        1               5                   10                  15

Glu Gly Val Glu Gly Asp Val Glu Thr Phe Leu Gly Ile Pro Phe Ala
```

-continued

```
                20                  25                  30
Ala Pro Pro Val Gly Asp Leu Arg Trp Arg Pro Ala Pro Pro Arg
                35                  40                  45
Ala Trp Ala Gly Thr Arg Asp Gly Arg Arg Phe Ala Pro Asp Cys Ile
    50                  55                  60
Gly Asp Glu Arg Leu Arg Glu Gly Ser Arg Ala Ala Gly Thr Ser Glu
65                  70                  75                  80
Asp Cys Leu Tyr Leu Asn Ile Trp Ser Pro Lys Gln Val Gly Lys Gly
                85                  90                  95
Gly Leu Pro Val Met Ile Trp Val Tyr Gly Gly Phe Ser Gly Gly
                100                 105                 110
Ser Gly Ala Val Pro Tyr Tyr Asp Gly Ser Ala Leu Ala Gln Lys Gly
            115                 120                 125
Val Val Val Val Thr Phe Asn Tyr Arg Ala Gly Ile Leu Gly Phe Leu
            130                 135                 140
Ala His Pro Ala Leu Ser Lys Glu Ser Pro Asn Gly Val Ser Gly Asn
145                 150                 155                 160
Tyr Gly Leu Leu Asp Met Leu Ala Ala Phe Lys Trp Val Gln Asn Asn
                165                 170                 175
Ile Arg Glu Phe Gly Gly Asp Pro Asn Arg Val Thr Val Phe Gly Glu
                180                 185                 190
Ser Ala Gly Ala Ser Ala Ile Gly Leu Leu Leu Thr Ser Pro Leu Ser
            195                 200                 205
Glu Ser Ala Phe Asn Gln Ala Ile Leu Gln Ser Pro Gly Leu Ala Arg
        210                 215                 220
Pro Leu Ala Thr Leu Ser Glu Ser Glu Ala Asn Gly Leu Glu Leu Gly
225                 230                 235                 240
Ala Asp Ile Ser Ala Leu Arg Arg Ala Asp Ala Gly Glu Leu Thr Lys
                245                 250                 255
Ile Ala Gln Ser Arg Ile Pro Met Ser Arg Gln Phe Thr Lys Pro Arg
            260                 265                 270
Pro Met Gly Pro Ile Leu Asp Gly Tyr Val Leu Arg Thr Leu Asp Val
        275                 280                 285
Asp Ala Phe Ala Lys Gly Ala Phe Arg Lys Ile Pro Val Ile Val Gly
        290                 295                 300
Gly Asn Ala Asp Glu Gly Arg Ala Phe Thr Asp Arg Leu Pro Val Lys
305                 310                 315                 320
Thr Val Leu Glu Tyr Arg Ala Tyr Leu Thr Glu Gln Phe Gly Asp Glu
                325                 330                 335
Ala Asp Ala Trp Glu Arg Cys Tyr Pro Ala Asn Ser Asp Ala Asp Val
            340                 345                 350
Pro Ala Ala Val Ala Arg Leu Phe Gly Asp Ser Gln Phe Asn Asn Gly
            355                 360                 365
Ile Glu Leu Leu Ser Ala Ala Phe Val Lys Trp Arg Thr Pro Leu Trp
        370                 375                 380
Arg Tyr Arg Phe Thr Gly Ile Pro Gly Pro Gly Arg Arg Pro Ala Thr
385                 390                 395                 400
His Gly Asp Glu Ile Pro Tyr Val Phe Ala Asn Leu Gly Pro Ser Ser
                405                 410                 415
Val Ala Val Phe Gly Ser Leu Ala Gly Val Gly Ala Ala Asp Ile
            420                 425                 430
Lys Leu Ala Ala Glu Met Ser Ser Ala Trp Val Ser Phe Ala Ala His
        435                 440                 445
```

```
Gly Val Pro Asp Gln Gly Thr Lys Ser His Trp Pro Arg Phe Asp Arg
    450                 455                 460

Arg Gly Glu Ile Met Thr Phe Gly Ser Gln Val Gly Ser Gly Glu Gly
465                 470                 475                 480

Leu Gly Val Ser Pro Ser Lys Ala Cys Gln Pro Ser Lys
                485                 490
```

<210> SEQ ID NO 38
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 38

```
Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
                20                  25                  30

Ala Pro Pro Val Gly Asp Leu Arg Trp Arg Pro Ala Pro Pro Arg
            35                  40                  45

Ala Trp Ala Gly Thr Arg Asp Gly Arg Arg Phe Ala Pro Asp Cys Ile
50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
290                 295                 300

Gly Asn Ala Asp Glu Gly Arg Ala Phe Thr Asp Arg Leu Pro Val Lys
305                 310                 315                 320
```

```
Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
            355                 360                 365

Ile Glu Leu Leu Ser Ala Ala Phe Val Lys Trp Arg Thr Pro Leu Trp
370                 375                 380

Arg Tyr Arg Phe Leu Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Gly Ala Gly Ala Ala Asp Ile
            420                 425                 430

Lys Leu Ala Thr Glu Met Ser Ala Ala Trp Val Ser Phe Ala Val His
            435                 440                 445

Gly Val Pro Asp Gln Gly Thr Lys Thr His Trp Pro Arg Phe Asp Ile
            450                 455                 460

Ser Gly Glu Ile Lys Thr Phe Gly Ser Gln Val Gly Ser Gly Glu Gly
465                 470                 475                 480

Leu Gly Val Ser Pro Ser Lys Ala Cys Gln Pro Ser Lys
                485                 490

<210> SEQ ID NO 39
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 39

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
            35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
            130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190
```

```
Ser Ala Gly Ala Ser Ala Ile Gly Leu Leu Thr Ser Pro Leu Ser
            195                 200                 205

Glu Ser Ala Phe Asn Gln Ala Ile Leu Gln Ser Pro Gly Leu Ala Arg
        210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
        290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Thr Gln Phe Asn Asn Gly
        355                 360                 365

Ile Glu Val Leu Ser Ala Ala Phe Val Lys Trp Arg Thr Pro Leu Trp
370                 375                 380

Arg Tyr Arg Phe Leu Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Val Phe Gly Ser Leu Ala Gly Gly Val Gly Ala Ala Asp Ile
            420                 425                 430

Lys Leu Ala Thr Glu Met Ser Ser Ala Trp Val Ser Phe Ala Ala His
        435                 440                 445

Gly Val Pro Asp Gln Gly Thr Lys Thr His Trp Pro Arg Phe Asp Ile
450                 455                 460

Arg Gly Glu Ile Lys Thr Phe Gly Ser Gln Val Gly Ser Gly Glu Gly
465                 470                 475                 480

Leu Gly Val Ser Pro Ser Lys Ala Cys Pro Pro Ser Lys
                485                 490

<210> SEQ ID NO 40
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 40

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Pro Ala Pro Pro Arg
        35                  40                  45

Ala Trp Ala Gly Thr Arg Asp Gly Arg Arg Phe Ala Pro Asp Cys Ile
    50                  55                  60
```

```
Gly Asp Glu Arg Leu Arg Glu Gly Ser Arg Ala Ala Gly Thr Ser Glu
 65                  70                  75                  80

Asp Cys Leu Tyr Leu Asn Ile Trp Ser Pro Lys Gln Val Gly Lys Gly
                 85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
            355                 360                 365

Ile Glu Leu Leu Ser Ala Ala Phe Val Lys Trp Arg Thr Pro Leu Trp
370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Met Phe Gly Ser Leu Ala Gly Ala Gly Ala Ala Asp Ile
            420                 425                 430

Lys Leu Ala Thr Glu Met Ser Ala Ala Trp Val Ser Phe Ala Ala His
            435                 440                 445

Gly Val Pro Asp Gln Gly Thr Lys Ser His Trp Pro Arg Phe Asp Arg
            450                 455                 460

Ser Gly Glu Ile Lys Thr Phe Gly Ser Gln Val Gly Ser Gly Glu Gly
465                 470                 475                 480
```

```
Leu Gly Val Ser Pro Ser Lys Ala Cys Pro Pro Ser Lys
            485                 490

<210> SEQ ID NO 41
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 41

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
        275                 280                 285

Asp Ala Phe Ala Lys Gly Ala Phe Arg Lys Ile Pro Val Ile Val Gly
    290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350
```

```
Pro Ala Ala Val Ala Arg Leu Phe Gly Asp Ser Gln Phe Asn Asn Gly
            355                 360                 365

Ile Glu Met Leu Ser Ala Ala Phe Val Lys Trp Arg Thr Pro Leu Trp
370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
            405                 410                 415

Val Ser Val Phe Gly Ser Leu Ala Gly Val Gly Ala Ala Asp Ile
                420                 425                 430

Lys Leu Ala Thr Glu Met Ser Ala Ala Trp Val Ser Phe Ala Val His
            435                 440                 445

Gly Val Pro Asp Gln Gly Thr Lys Ser His Trp Pro Arg Phe Asp Arg
    450                 455                 460

Ser Gly Glu Ile Lys Thr Phe Gly Ser Gln Val Gly Ser Gly Glu Gly
465                 470                 475                 480

Leu Gly Val Ser Pro Ser Asn Ala Cys Pro Pro Ser Lys
                485                 490

<210> SEQ ID NO 42
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 42

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
    130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
        195                 200                 205

Glu Ser Ala Phe Asn Gln Ala Ile Leu Gln Ser Pro Gly Leu Ala Arg
    210                 215                 220
```

```
Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
            245                 250                 255

Ile Ala Gln Ser Arg Ile Pro Met Ser Arg Gln Phe Thr Lys Pro Arg
        260                 265                 270

Pro Met Gly Pro Ile Leu Asp Gly Tyr Val Leu Arg Thr Leu Asp Val
    275                 280                 285

Asp Ala Phe Ala Lys Gly Ala Phe Arg Lys Ile Pro Val Ile Val Gly
290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
        355                 360                 365

Ile Glu Met Leu Ser Ala Ala Phe Val Lys Trp Arg Thr Pro Leu Trp
370                 375                 380

Arg Tyr Arg Phe Thr Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ser Val Phe Gly Ser Leu Ala Gly Gly Val Gly Ala Ala Asp Ile
            420                 425                 430

Lys Leu Ala Thr Glu Met Ser Ala Ala Trp Val Ser Phe Ala Ala His
        435                 440                 445

Gly Val Pro Asp Arg Gly Thr Lys Ser His Trp Pro Arg Phe Asp Arg
    450                 455                 460

Ser Gly Glu Ile Lys Thr Phe Gly Ser Gln Val Gly Ser Gly Glu Gly
465                 470                 475                 480

Leu Gly Val Ser Pro Ser Asn Ala Cys Pro Pro Ser Lys
                485                 490

<210> SEQ ID NO 43
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 43

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Pro Ala Pro Pro Arg
        35                  40                  45

Ala Trp Ala Gly Thr Arg Asp Gly Arg Arg Phe Ala Pro Asp Cys Ile
    50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95
```

```
Gly Leu Pro Val Met Ile Trp Val Tyr Gly Gly Phe Ser Gly Gly
                100                 105                 110

Ser Gly Ala Val Pro Tyr Tyr Asp Gly Ser Ala Leu Ala Gln Lys Gly
        115                 120                 125

Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
                180                 185                 190

Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
                260                 265                 270

Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
                340                 345                 350

Pro Ala Ala Val Ala Arg Leu Phe Gly Asp Ser Gln Phe Asn His Gly
            355                 360                 365

Ile Glu Val Leu Ser Ala Ala Phe Val Lys Trp Arg Thr Pro Leu Trp
370                 375                 380

Arg Tyr Arg Phe Leu Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ala Val Phe Gly Ser Leu Ala Gly Val Gly Pro Ala Asp Ile
            420                 425                 430

Lys Leu Ala Ala Glu Met Ser Ser Ala Trp Val Ser Phe Ala Ala His
        435                 440                 445

Gly Val Pro Asp Gln Gly Thr Lys Thr His Trp Pro Arg Phe Asp Ile
        450                 455                 460

Ser Gly Glu Ile Lys Thr Phe Gly Ser Gln Val Gly Ser Gly Glu Gly
465                 470                 475                 480

Leu Gly Val Ser Pro Ser Lys Ala Cys Pro Pro Ser Lys
                485                 490

<210> SEQ ID NO 44
<211> LENGTH: 493
<212> TYPE: PRT
```

<213> ORGANISM: Artificial sequence
<220> FEATURE:
<223> OTHER INFORMATION: Polypeptidvariante der SEQ ID-Nr. 1

<400> SEQUENCE: 44

```
Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Lys Gly
            85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
            115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
            165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Leu Thr Ser Pro Leu Ser
            195                 200                 205

Glu Ser Ala Phe Asn Gln Ala Ile Leu Gln Ser Pro Gly Leu Ala Arg
            210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
            245                 250                 255

Ile Ala Gln Ser Arg Ile Pro Met Ser Arg Gln Phe Thr Lys Pro Arg
            260                 265                 270

Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
            290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
            325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn Asn Gly
            355                 360                 365

Ile Glu Met Leu Ser Ala Ala Phe Val Lys Trp Arg Thr Pro Leu Trp
            370                 375                 380

Arg Tyr Arg Phe Leu Gly Ile Pro Gly Pro Gly Arg Arg Pro Ala Thr
```

```
385             390             395             400
His Gly Asp Glu Ile Pro Tyr Val Phe Ala Asn Leu Gly Pro Ser Ser
                405                 410                 415

Val Ser Val Phe Gly Ser Leu Ala Gly Val Gly Ala Ala Asp Ile
            420                 425                 430

Lys Leu Ala Ala Glu Met Ser Ala Ala Trp Val Ser Phe Ala Ala His
                435                 440                 445

Gly Val Pro Asp Arg Gly Thr Gln Ser His Trp Pro Arg Tyr Asp Arg
            450                 455                 460

Ser Gly Glu Ile Lys Thr Phe Gly Ser Gln Val Gly Ser Glu Gly
465                 470                 475                 480

Leu Gly Val Ser Pro Ser Asn Ala Cys Pro Pro Ser Lys
                485                 490

<210> SEQ ID NO 45
<211> LENGTH: 493
<212> TYPE: PRT
<213> ORGANISM: Artificial sequence
<220> FEATURE:
<223> OTHER INFORMATION: Polypeptidvariante der SEQ ID-Nr. 1

<400> SEQUENCE: 45

Gln Thr Asp Asp Pro Lys Leu Val Arg His Thr Gln Ser Gly Ala Val
1               5                   10                  15

Glu Gly Val Glu Gly Asp Val Glu Thr Phe Leu Gly Ile Pro Phe Ala
            20                  25                  30

Ala Pro Pro Val Gly Asp Leu Arg Trp Arg Pro Ala Pro Pro Arg
        35                  40                  45

Ala Trp Ala Gly Thr Arg Asp Gly Arg Arg Phe Ala Pro Asp Cys Ile
50                  55                  60

Gly Asp Glu Arg Leu Arg Glu Gly Ser Arg Ala Ala Gly Thr Ser Glu
65                  70                  75                  80

Asp Cys Leu Tyr Leu Asn Ile Trp Ser Pro Lys Gln Val Gly Lys Gly
                85                  90                  95

Gly Leu Pro Val Met Ile Trp Val Tyr Gly Gly Gly Phe Ser Gly Gly
            100                 105                 110

Ser Gly Ala Val Pro Tyr Tyr Asp Gly Ser Ala Leu Ala Gln Lys Gly
        115                 120                 125

Val Val Val Val Thr Phe Asn Tyr Arg Ala Gly Ile Leu Gly Phe Leu
130                 135                 140

Ala His Pro Ala Leu Ser Lys Glu Ser Pro Asn Gly Val Ser Gly Asn
145                 150                 155                 160

Tyr Gly Leu Leu Asp Met Leu Ala Ala Phe Lys Trp Val Gln Asn Asn
                165                 170                 175

Ile Arg Glu Phe Gly Gly Asp Pro Asn Arg Val Thr Val Phe Gly Glu
            180                 185                 190

Ser Ala Gly Ala Ser Ala Ile Gly Leu Leu Thr Ser Pro Leu Ser
        195                 200                 205

Glu Ser Ala Phe Asn Gln Ala Ile Leu Gln Ser Pro Gly Leu Ala Arg
210                 215                 220

Pro Leu Ala Thr Leu Ser Glu Ser Glu Ala Asn Gly Leu Glu Leu Gly
225                 230                 235                 240

Ala Asp Ile Ser Ala Leu Arg Arg Ala Asp Ala Gly Glu Leu Thr Lys
                245                 250                 255

Ile Ala Gln Ser Arg Ile Pro Met Ser Arg Gln Phe Thr Lys Pro Arg
```

```
                260                 265                 270
Pro Met Gly Pro Ile Leu Asp Gly Tyr Val Leu Arg Thr Leu Asp Val
            275                 280                 285

Asp Ala Phe Ala Lys Gly Ala Phe Arg Lys Ile Pro Val Ile Val Gly
        290                 295                 300

Gly Asn Ala Asp Glu Gly Arg Ala Phe Thr Asp Arg Leu Pro Val Lys
305                 310                 315                 320

Thr Val Leu Glu Tyr Arg Ala Tyr Leu Thr Glu Gln Phe Gly Asp Glu
                325                 330                 335

Ala Asp Ala Trp Glu Arg Cys Tyr Pro Ala Asn Ser Asp Ala Asp Val
            340                 345                 350

Pro Ala Ala Val Ala Arg Leu Phe Gly Asp Ser Gln Phe Asn His Gly
        355                 360                 365

Ile Glu Val Leu Ser Ala Ala Phe Val Lys Trp Arg Thr Pro Leu Trp
    370                 375                 380

Arg Tyr Arg Phe Leu Gly Ile Pro Gly Pro Gly Arg Arg Pro Ala Thr
385                 390                 395                 400

His Gly Asp Glu Ile Pro Tyr Val Phe Ala Asn Leu Gly Pro Ser Ser
                405                 410                 415

Val Ala Val Phe Gly Ser Leu Ala Gly Val Gly Pro Ala Asp Ile
            420                 425                 430

Lys Leu Ala Ala Glu Met Ser Ser Ala Trp Val Ser Phe Ala Ala His
        435                 440                 445

Gly Val Pro Asp Arg Gly Thr Gln Thr His Trp Pro Arg Tyr Asp Ile
    450                 455                 460

Ser Gly Glu Ile Lys Thr Phe Gly Ser Gln Val Gly Ser Gly Glu Gly
465                 470                 475                 480

Leu Gly Val Ser Pro Ser Asn Ala Cys Pro Pro Ser Lys
                485                 490

<210> SEQ ID NO 46
<211> LENGTH: 540
<212> TYPE: PRT
<213> ORGANISM: Sphingopyxis sp.

<400> SEQUENCE: 46

Val Lys Glu His Gln Cys Arg Gly Gly Arg Ala Ser Pro Ala Ala Pro
1               5                   10                  15

Ala Thr Trp Leu Ala Arg Ile Ser Val Ser Arg Gly Ala Ser Ala Ile
            20                  25                  30

Ala Trp Thr Phe Met Leu Gly Ala Thr Ala Ile Pro Val Ala Ala Gln
        35                  40                  45

Thr Asp Asp Pro Lys Leu Val Arg His Thr Gln Ser Gly Ala Val Glu
    50                  55                  60

Gly Val Glu Gly Asp Val Glu Thr Phe Leu Gly Ile Pro Phe Ala Ala
65                  70                  75                  80

Pro Pro Val Gly Asp Leu Arg Trp Arg Pro Ala Pro Pro Arg Ala
                85                  90                  95

Trp Ala Gly Thr Arg Asp Gly Arg Arg Phe Ala Pro Asp Cys Ile Gly
            100                 105                 110

Asn Glu Arg Leu Arg Glu Gly Ser Arg Ala Ala Gly Thr Ser Glu Asp
        115                 120                 125

Cys Leu Tyr Leu Asn Ile Trp Ser Pro Lys Gln Val Gly Lys Gly Gly
    130                 135                 140
```

```
Leu Pro Val Met Ile Trp Val Tyr Gly Gly Phe Ser Gly Gly Ser
145                 150                 155                 160

Gly Ala Val Pro Tyr Tyr Asp Gly Ser Ala Leu Ala Gln Lys Gly Val
            165                 170                 175

Val Val Val Thr Phe Asn Tyr Arg Ala Gly Ile Leu Gly Phe Leu Ala
            180                 185                 190

His Pro Ala Leu Ser Lys Glu Ser Pro Asn Gly Val Ser Gly Asn Tyr
            195                 200                 205

Gly Leu Leu Asp Met Leu Ala Ala Phe Lys Trp Val Gln Asn Asn Ile
            210                 215                 220

Arg Glu Phe Gly Gly Asp Pro Asn Arg Val Thr Val Phe Gly Glu Ser
225                 230                 235                 240

Ala Gly Ala Ser Ala Leu Gly Leu Leu Leu Thr Ser Pro Leu Ser Glu
            245                 250                 255

Ser Ala Phe Asn Gln Ala Ile Leu Gln Ser Pro Gly Leu Ala Arg Pro
            260                 265                 270

Leu Ala Thr Leu Ser Glu Ser Glu Ala Asn Gly Leu Glu Leu Gly Ala
            275                 280                 285

Asp Ile Ser Ala Leu Arg Arg Ala Asp Ala Gly Glu Leu Thr Lys Ile
            290                 295                 300

Ala Gln Ser Arg Ile Pro Met Ser Arg Gln Phe Thr Lys Pro Arg Pro
305                 310                 315                 320

Met Gly Pro Ile Leu Asp Gly Tyr Val Leu Arg Thr Leu Asp Val Asp
            325                 330                 335

Ala Phe Ala Lys Gly Ala Phe Arg Lys Ile Pro Val Leu Val Gly Gly
            340                 345                 350

Asn Ala Asp Glu Gly Arg Ala Phe Thr Asp Arg Leu Pro Val Lys Thr
            355                 360                 365

Val Leu Glu Tyr Arg Ala Tyr Leu Thr Glu Gln Phe Gly Asp Glu Ala
            370                 375                 380

Asp Ala Trp Glu Arg Cys Tyr Pro Ala Asn Ser Asp Ala Asp Val Pro
385                 390                 395                 400

Ala Ala Val Ala Arg Leu Phe Gly Asp Ser Gln Phe Asn Asn Gly Ile
            405                 410                 415

Glu Leu Leu Ser Ala Ala Phe Ala Lys Trp Arg Thr Pro Leu Trp Arg
            420                 425                 430

Tyr Arg Phe Thr Gly Ile Pro Gly Ala Gly Arg Arg Pro Ala Thr His
            435                 440                 445

Gly Asp Glu Ile Pro Tyr Val Phe Ala Asn Leu Gly Pro Ser Ser Val
            450                 455                 460

Ser Met Phe Gly Ser Leu Glu Gly Gly Ala Gly Ala Ser Asp Ile Lys
465                 470                 475                 480

Leu Ala Thr Glu Met Ser Ala Ala Trp Val Ser Phe Ala Val His Gly
            485                 490                 495

Val Pro Asp Gln Gly Thr Lys Ser His Trp Pro Arg Phe Glu Arg Arg
            500                 505                 510

Gly Glu Ile Met Thr Phe Gly Ser Gln Val Gly Ser Gly Glu Gly Leu
            515                 520                 525

Gly Val Ser Pro Ser Lys Ala Cys Gln Pro Ser Lys
            530                 535                 540
```